(12) United States Patent
Li et al.

(10) Patent No.: US 8,232,407 B2
(45) Date of Patent: Jul. 31, 2012

(54) NITROGENOUS HETEROCYCLIC COMPOUNDS WITH INSECTICIDAL ACTIVITY, AND THE PREPARATION AND USE THEREOF

(75) Inventors: Zhong Li, Shanghai (CN); Xuhong Qian, Shanghai (CN); Xusheng Shao, Shanghai (CN); Xiaoyong Xu, Shanghai (CN); Liming Tao, Shanghai (CN); Gonghua Song, Shanghai (CN); Qingchun Huang, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 132 days.

(21) Appl. No.: 12/864,410

(22) PCT Filed: May 28, 2008

(86) PCT No.: PCT/CN2008/071115
§ 371 (c)(1),
(2), (4) Date: Jul. 23, 2010

(87) PCT Pub. No.: WO2009/094867
PCT Pub. Date: Aug. 6, 2009

(65) Prior Publication Data
US 2010/0298346 A1    Nov. 25, 2010

(30) Foreign Application Priority Data

Jan. 23, 2008   (CN) .......................... 2008 1 0032949

(51) Int. Cl.
*C07D 407/14* (2006.01)
*A61K 31/44* (2006.01)
(52) U.S. Cl. .................................. 546/275.1; 514/341
(58) Field of Classification Search ............ 546/275.1; 514/341
See application file for complete search history.

(56) References Cited

FOREIGN PATENT DOCUMENTS

| | | |
|---|---|---|
| EP | 0192060 | 8/1986 |
| EP | 0235725 | 9/1987 |
| EP | 0244777 | 11/1987 |
| EP | 0247477 | 12/1987 |
| EP | 0296453 | 12/1988 |
| EP | 0315826 | 5/1989 |
| EP | 0386565 | 9/1990 |
| EP | 0580553 | 1/1994 |
| EP | 0685477 | 12/1995 |
| EP | 1031566 | 8/2000 |
| JP | 62-292765 | 12/1987 |
| JP | 07-242633 | 9/1995 |
| JP | 08-259568 | 10/1996 |
| JP | 08-291171 | 11/1996 |
| WO | 2004/056178 | 7/2004 |
| WO | 2004/058714 | 7/2004 |

OTHER PUBLICATIONS

Shao et al. (J. Agric. Food Chem. 2009, 57, 951-957).*
International Search Report of PCT/CN2008/071115, dated Oct. 30, 2008.

* cited by examiner

*Primary Examiner* — Robert Havlin
(74) *Attorney, Agent, or Firm* — Hamre, Schumann, Mueller & Larson, P.C.

(57) ABSTRACT

The present invention relates to nitro-containing heterocyclic or ring-opening nitrogenous compounds of formula (A), wherein $R_1$, $R_2$, $R_3$, $R_4$, $R_5$, Y, Z, and W are as defined in the specification. The present invention discloses the preparation and the uses of a novel insecticide. Said compound and the derivatives thereof have high insecticidal activity to farm insects including homoptera and lepidoptera pests, such as aphis, fulgorides, aleyrodids, leafhopper, commom thrips, cotton bollworm, cabbage caterpillar, cabbage moth, cotton leafworm, armyworn and so on.

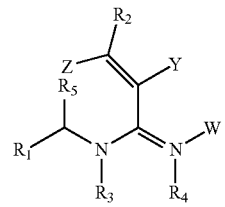

(A)

13 Claims, No Drawings

NITROGENOUS HETEROCYCLIC COMPOUNDS WITH INSECTICIDAL ACTIVITY, AND THE PREPARATION AND USE THEREOF

FIELD OF THE INVENTION

This invention relates to novel neonicotinoid insecticides, and the preparation and uses thereof.

BACKGROUND OF THE INVENTION

The first neonicotinoid insecticide, Imidacloprid, which was developed by Bayer AG in middle 1980s, has been one of the most successful novel insecticides. Represented by Imidacloprid, the neonicotinoid insecticides were featured with high insecticidal activities, broad insecticidal spectra, low mammalian and aquatic toxicity, favorable systemic properties, proper field stability, and environmental friendliness. Therefore, the neonicotinoid insecticides have become one of the most important hot areas in insecticidal innovation. Afterwards, a series of neonicotinoid insecticides, such as Thiacloprid, Clothianidin, Thiamethoxam, Acetamiprid, Nitenpyram and Dinotefuran, were developed (EP 247477, 296453, 685477, 235725, 235725, 315826, 192060, 244777, 0386565, 580553, and 1031566, JP 62292765, 8259568, 8291171, and 7242633).

However, the application of these compounds was somehow limited due to the serious resistance caused by frequent use of and cross-resistance between these neonicotinoid insecticides having high structural similarity, which were also the important reasons that restrict further development of neonicotinoid insecticides. Meanwhile, the selectivity for insect control was limited by a narrow insecticide controlling spectrum as the neonicotinoid insecticides were mainly high active on Homoptera and Lepidoptera pests.

Thus, the main technical problem to be solved by the present invention is to develop novel and more effective insecticides by the structural modification of nitromethylene compounds so as to resolve the resistance issue, broaden the insecticidal spectrum and make the novel compounds applicable as insecticides.

SUMMARY OF THE INVENTION

The object of this invention is to provide effective pest control compounds and a method for the preparation thereof The other object of this invention is to provide the protection for growing and harvested plants against insect.

According to the first aspect of this invention, there is provided a compound of formula (A), or the optical isomer, cis-trans isomer, or insecticidal acceptable salt thereof,

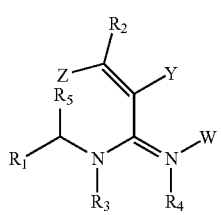

(A)

wherein
$R_1$ is an unsubstituted or halogenated 5 or 6 membered heterocycle interrupted by nitrogen, oxygen and/or sulfur atom(s), substituted or unsubstituted phenyl group. The substituents are one or more groups selected from halogen atom, $C_{1-4}$ haloalkyl and $C_{1-4}$ chloroalkoxyl;

$R_2$ is a hydrogen atom, $C_{1-6}$ alkyl group, or $C_{1-6}$ alkyl group substituted by F, Cl or Br.

$R_3$ and $R_4$ are independently selected from hydrogen atom, $C_{1-6}$ alkyl, allyl, benzyl, $C_{1-4}$ alkoxyl-$C_{1-4}$ alkyl, $C_{1-4}$ alkoxyl-carbonyl, phenoxylcarbonyl, $C_{2-6}$ alkynyl-carbonyl, $C_{2-3}$ alkenyl-carbonyl, $C_{3-6}$ cycloalkyl-carbonyl, furan carbonyl, N,N'-dimethyl carbonyl, unsubstituted benzoyl group or benzoyl substituted by one or more groups selected from halogen atom, $C_{1-4}$ alkyl, $C_{1-4}$ haloalkyl, $C_{1-4}$ alkoxyl and $C_{1-4}$ alkyl-carbonyl, or $R_3$ and $R_4$ taken together forms —$CH_2$—$CH_2$— or —$CH_2$—$CH_2$—$CH_2$—;

$R_5$ is a hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;

W is absent, or when $R_3$ and $R_4$ taken together forms a —$CH_2$—$CH_2$— or —$CH_2$—$CH_2$—$CH_2$—, W is $R_6$ and conforms onium salt with $X^-$ together with the nitrogen atom connected with $R_6$, wherein $R_6$ is a hydrogen atom, saturated or unsaturated $C_{1-6}$ hydrocarbon group, saturated or unsaturated halogenated $C_{1-6}$ hydrocarbon, or saturated or unsaturated $C_{1-6}$ alkoxyl;

$X^-$ is $F^-$, $Cl^-$, $Br^-$, $I^-$, $NO_3^-$, $SO_4^-$, $AcO^-$, or $PhCOO^-$;

Y is a nitro or cyano;

Z is a substituted or unsubstituted phenyl, substituted or unsubstituted 5 or 6 membered heterocycle interrupted by nitrogen, oxygen and/or sulfur atom(s), substituted or unsubstituted $C_{5-12}$ heteroaryl, wherein the substituents are one or more groups selected from:

halogen atom, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl or phenyl group substituted by one or more groups selected from:

halogen atom, $C_{1-4}$ alkyl, $C_{1-4}$ haloalkyl, $C_{1-4}$ alkoxyl, $C_{1-4}$ alkyl-carbonyl, $C_{1-4}$ alkylamino and $C_{1-4}$ alkoxyl-carbonyl.

In one of the embodiments, the compound has the structure selected from the following formulas:

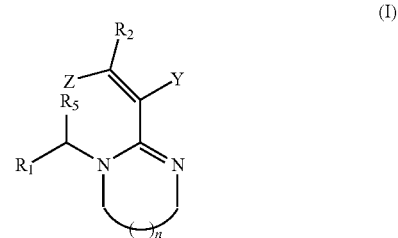

(I)

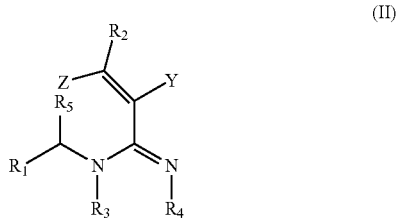

(II)

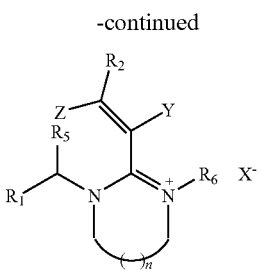

Wherein $R_1, R_2, R_3, R_4, R_5, R_6, Y, Z$ are as defined above, and n is 0 or 1.

In one preferred example, n is 0.
In another preferred example, in the above formulas:
$R_1$ represents an unsubstituted or halogenated 5 or 6 membered heterocycle interrupted by nitrogen, oxygen and/or sulfur atom(s);
$R_2$ represents a hydrogen atom, unsubstituted $C_{1-6}$ alkyl, or a $C_{1-6}$ alkyl substituted by fluoro, chloro or bromo;
$R_3$ and $R_4$ independently represent hydrogen atom, $C_{1-6}$ alkyl, allyl, benzyl, $C_{1-4}$ alkoxyl-$C_{1-4}$ alkyl, $C_{1-4}$ alkoxyl-carbonyl, phenoxy-carbonyl, $C_{2-6}$ alkynyl-carbonyl, $C_{2-3}$ alkenyl-carbonyl, $C_{3-6}$ cycloalkyl-carbonyl, furan carbonyl, N,N'-dimethyl carbonyl, unsubstituted benzoyl or benzoyl substituted by one or more groups selected from halogen atom, $C_{1-4}$ alkyl, $C_{1-4}$ haloalkyl, $C_{1-4}$ alkoxyl and $C_{1-4}$ alkyl-carbonyl;
$R_5$ and $R_6$ represent hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;
$X^-$ represents $Cl^-$, $Br^-$, $I^-$, $NO_3^-$, $SO_4^-$, $AcO^-$, or $PhCOO^-$;
Y represents nitro or cyano group;
Z represents substituted or unsubstituted phenyl, substituted or unsubstituted 5 or 6 membered heterocycle containing nitrogen, oxygen and/or sulfur atom(s), substituted or unsubstituted $C_{5-12}$ heteroaryl group, wherein the substituents are one or more groups selected from: halogen atoms, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl and phenyl substituted by one or more groups selected from:
halogen atom, $C_{1-4}$ alkyl, $C_{1-4}$ haloalkyl, $C_{1-4}$ alkoxyl, $C_{1-4}$ alkyl-carbonyl, $C_{1-4}$ alkylamino and $C_{1-4}$ alkoxyl-carbonyl;
n represents 0 or 1.
In another embodiment, $R_1$ is selected from pyridyl, thiazolyl, pyrimidinyl, tetrahydrofuryl, oxazolyl, or the halides thereof.
In one preferred example, $R_1$ represents halopyridyl, halothiazolyl, halopyrimidinyl, halotetrahydrofuryl, halooxazolyl, and more preferably chlorides.
In another preferred example, $R_1$ represents

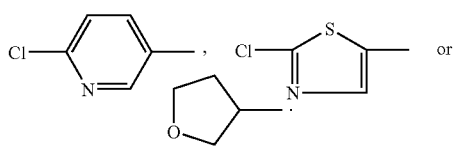

In another embodiment, $R_2$ is hydrogen atom or $C_{1-6}$ alkyl.
In one preferred example, $R_2$ represents hydrogen atom or $C_{1-3}$ alkyl, more preferably hydrogen atom or methyl, and even more preferably hydrogen atom.

In another embodiment, $R_3$ and $R_4$ are hydrogen atom or $C_{1-6}$ alkyl.
In one preferred example, $R_3$ and $R_4$ represent hydrogen atom or $C_{1-3}$ alkyl, and preferably hydrogen atom, methyl or ethyl.
In another embodiment, $R_5$ is hydrogen atom or $C_{1-6}$ alkyl.
In one preferred example, $R_5$ represents hydrogen atom or $C_{1-3}$ alkyl, and preferably hydrogen atom, methyl or ethyl.
In another embodiment, $R_6$ is hydrogen atom, saturated or unsaturated $C_{1-3}$ hydrocarbon group, saturated or unsaturated halogenated $C_{1-3}$ hydrocarbon group, saturated or unsaturated $C_{1-3}$ alkoxyl; $X^-$ represents $F^-$, $Cl^-$, $Br^-$, $I^-$, $NO_3^-$, $SO_4^-$, $AcO^-$, or $PhCOO^-$.
In another embodiment, Z is selected from substituted or unsubstituted furyl, thienyl, pyrrolyl, imidazolyl, thiazolyl, and oxazolyl, and wherein the substituents are selected from halogen atoms, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl, and phenyl group substituted by one or more groups selected from halogen atoms, $C_{1-4}$ alkyl, $C_{1-4}$ haloalkyl, $C_{1-4}$ alkoxyl, $C_{1-4}$ alkyl-carbonyl, $C_{1-4}$ alkylamino and $C_{1-4}$ alkoxyl-carbonyl.
In one preferred example, Z represents substituted or unsubstituted furyl, thienyl, or pyrrolyl group. Preferably, Z represents:

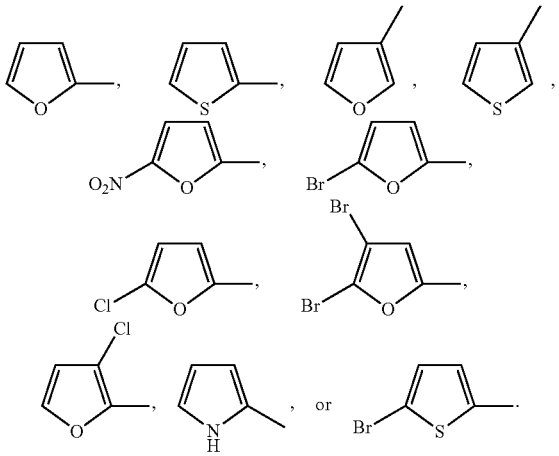

More preferably, Z represents

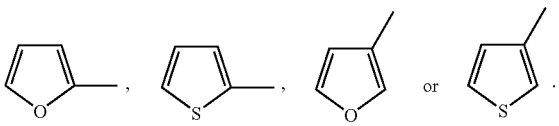

The above preferred substitutes can be combined to form preferred compounds of the present invention.

According to the second aspect of this invention, there is provided an insecticidal composition comprising: (a) 0.0001 wt %-99.9 wt % of the compound of the present invention, or the optical isomer, cis-trans isomer or insecticidal acceptable salt thereof, or the combinations thereof; and (b) insecticidal acceptable carrier(s) and/or excipient(s).

In one preferred example, the amount of component (a) is 0.01-99.9 wt %, more preferably 0.05-90 wt %, based on the total weight of the insecticidal composition.

In one embodiment, the composition is used to kill or control the insects chosen from: Coleoptera, Lepidoptera, Hemiptera, Orthoptera, Isoptera or Dipteral pests, preferably Isoptera or Lepidoptera pests.

In one preferred example, the pests have piercing-sucking type or rasping type mouthparts. In another preferred example, the pests are chosen from aphid, plant hopper, white fly, leaf hopper, thrips, cotton bollworm, Cabbage caterpillar, Diamondback moth, prodenia litura or army worm.

In another preferred example, the insecticidal composition further comprises other active substances selected from insecticide, co-bait, bactericide, acaricide, nematicide, or growth control agents.

According to the third aspect of this invention, there is provided a method for killing and controlling pests which comprises the step of applying the insecticidal composition to plants or the surrounding fields or environment thereof that attacked or possible to be attacked by the pests.

According to the fourth aspect of this invention, there is provided the use of the compounds of formula (I), or the optical isomer, cis-trans isomer, insecticidal acceptable salt thereof, or the combinations thereof, in the preparation of an insecticide composition.

In one preferred example, there is provided a use of the compound of formula (I), or the optical isomer, cis-trans isomer, or insecticidal acceptable salt thereof, or the combinations thereof in killing or controlling pests.

According to the fifth aspect of this invention, there is provided a method for the preparation of the compound of formula (I), or the optical isomer, cis-trans isomer, or insecticidal acceptable salt thereof, wherein said methods include the following steps:

in the presence of catalytic amount of acid, obtaining compound A by the addition of compound (a) with aldehyde (b) or ketone (c) at 0-60° C.

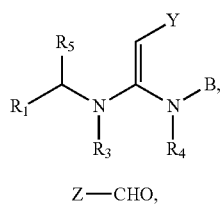

(a)

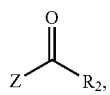

(b)

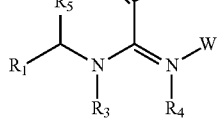

(c)

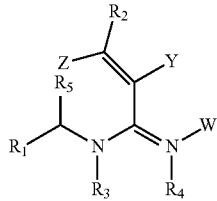

(A)

wherein, $R_1$, $R_2$, $R_3$, $R_4$, $R_5$, W, Y and Z are as defined above, B represents hydrogen atom or $R_6$ which is as defined above; provided that when W is $R_6$ in formula (A), the method further comprises the step of obtaining an onium salt by further reacting compound (A) with an acid comprising $X^-$, wherein $X^-$ is defined above.

In one preferred example, the reaction temperature is 15-45° C. More preferably, the temperature is 20-30° C. In another preferred example, the solvent is acetonitrile or ethanol. More preferably, the solvent is acetonitrile. In another preferred example, the acid in a catalytic amount is chosen from concentrated hydrochloric acid, concentrated sulfuric acid, and benzoic acid. More preferably, the catalytic acid is concentrated hydrochloric acid.

In another embodiment, the compound has the structure of formula (I), (II) or (III), and a method for the preparation of such a compound includes the following steps:

in the presence of catalytic amount of acid, carrying out the reaction as indicated below at 20-30° C. in acetonitrile for 2-24 hours to obtain the compound of formula (I):

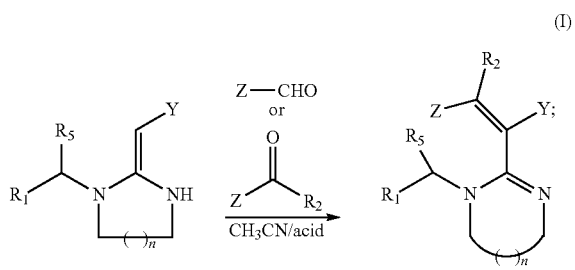

in the presence of catalytic amount of acid, carrying out the reaction as indicated below at 20-30° C. in acetonitrile for 2-24 hours to obtain the compound of formula (II):

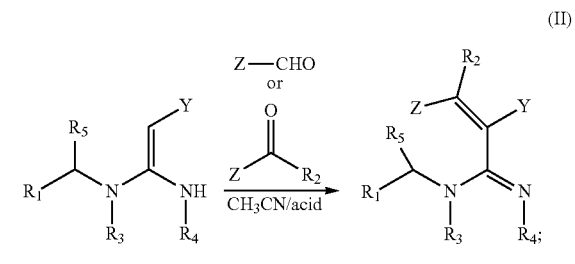

in the presence of catalytic amount of acid, carrying out the reaction as indicated below at 10-50° C. in acetonitrile for 2-24 hours to obtain the compound of formula (III):

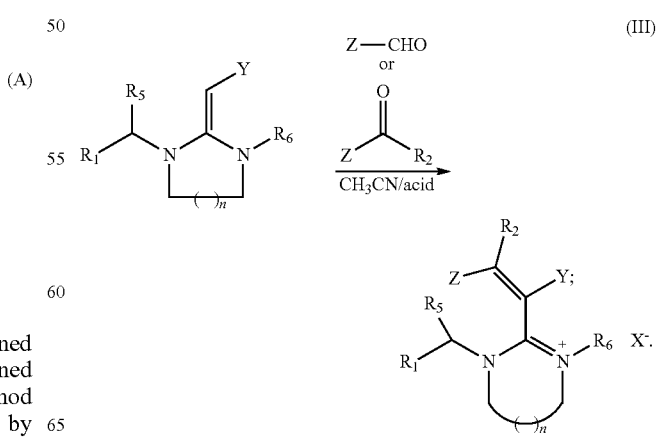

MODE OF CARRYING OUT THE INVENTION

Under long term deep investigation, this invention provides a novel neonicotinoid compound, which is obtained by introducing aromatic heterocycle to the nitromethylene group of known nitromethylene neonicotinoid insecticides, as well as changing the normal nitromethylene or cyanomethylene group in neonicotinoid compounds by shifting the double bond. The novel compound of the present invention shows remarkably increased insecticidal activity and broader insecticidal spectrum. Based on the above investigation, the invention was completed.

Definition of the Substituents

As used herein, the term "$C_{1-6}$ hydrocarbon group" refers to saturated or unsaturated substituents consisting of hydrogen and 1-6 carbons, such as alkyl, alkenyl, alkynyl, cycloalkyl, cyclo-alkenyl and aryl, preferably alkyl, alkenyl and alkynyl. The term "alkenyl" refers to a straight or branched alkenyl with 2-6 carbons atoms, such as vinyl, allyl, 1-propenyl, isopropenyl, 1-butenyl, 2-butenyl or other similar groups. The term "alkynyl" refers to straight or branched alkynyl with 2-6 carbons atoms, such as ethinyl and propargyl. The term "cycloalkyl" refers to cyclopropyl, cyclobutyl, cyclopentyl, cyclohexyl, cycloheptyl, and so on.

The term "$C_{1-6}$ alkyl" refers to straight or branched alkyl with 1-6 carbon atoms, such as methyl, ethyl, propyl, iso-propyl, butyl, iso-butyl, sec-butyl, tert-butyl or other similar groups.

The term "$C_{1-6}$ alkoxyl" refers to straight or branched alkoxyl with 1-6 carbon atoms, such as methoxyl, ethoxyl, propoxyl, iso-propoxyl, butoxyl, iso-butoxyl, sec-butoxyl, tert-butoxyl or other similar groups.

The term "halogen" refers to fluorine, chlorine, bromine or iodine. The term "halogenated" refers to substituents substituted by one or more same or different halogen atoms as mentioned above, such as trifluoromethyl, pentafluoroethyl, or other similar groups.

The term "$C_{5-12}$ aryl" refers to aromatic hydrocarbon group with single to triple rings, such as phenyl, naphthyl or other similar groups.

The term "aralkyl" refers to $C_{1-6}$ alkyl substituted by aryl(s) as mentioned above.

The term "5 or 6 membered heterocyclic group" refers to 5 or 6 membered cyclic group interrupted by one or more heteroatoms selected from nitrogen, oxygen or sulfur, such as pyridyl, thiazolyl, pyrimidinyl, tetrahydrofuryl and oxazolyl.

Methods for the Preparation of the Inventive Compounds

Compound of this invention can be synthesized as described above. The skilled in the art can synthesize the compound of formula (a) used in the reaction according to the prior art, such as WO2006056108A1 and WO2007101369A1.

In one particular embodiment of the present invention, a compound of formula (I) can be synthesized by the following procedure:

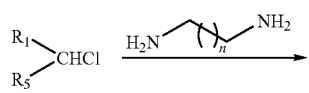

(I)

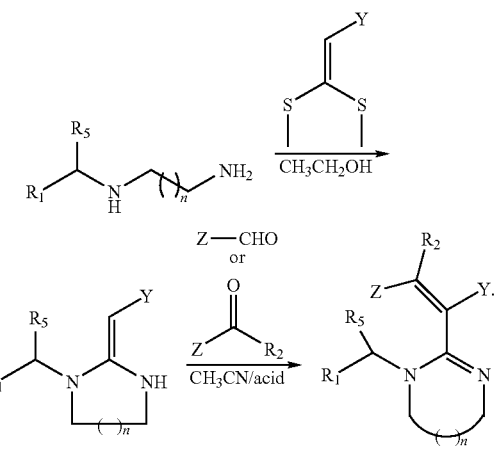

In other particular embodiments, a compound of formula (II) can be synthesized by the following procedure:

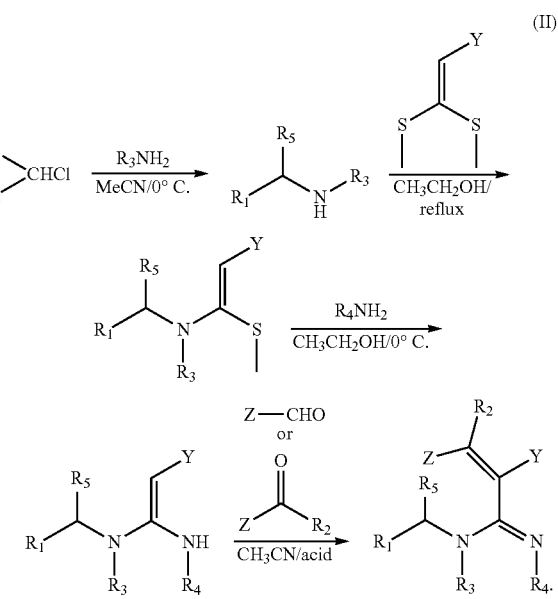

(II)

In other particular embodiments, a compound of formula (III) can be synthesized by the following procedure:

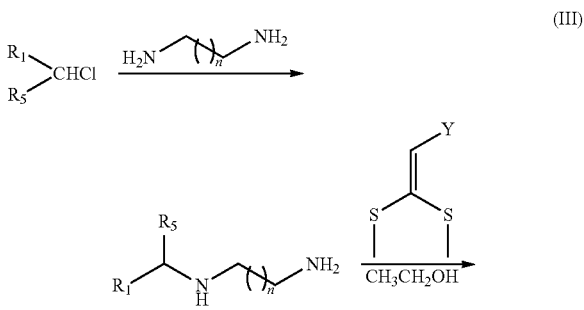

(III)

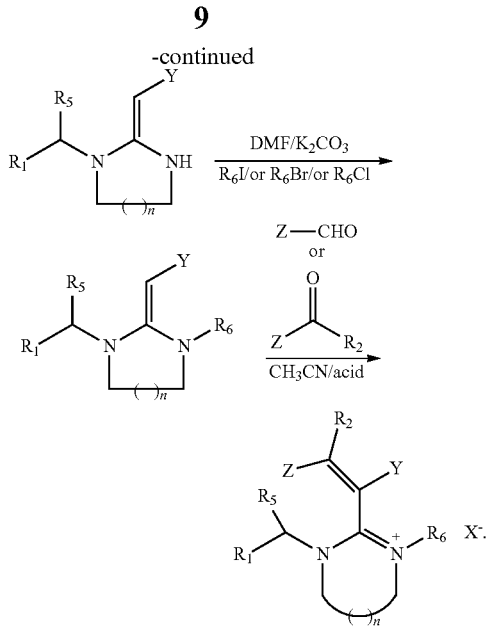

In one particular embodiment, a compound of formula (I) can be synthesized by the following procedure:

(1): A solution of 2-chloro-5-chloromethyl pyridine in acetonitrile is added dropwise to a diamine solution whose mole amount is 5-10 times that of 2-chloro-5-(chloromethyl) pyridine. The reaction is carried out at 0-50° C. for 5-10 hours. After the reaction is completed, the mixture is distillated under reduced pressure to remove diamine, dissolved in ethyl acetate, and evaporated to obtain $N^1$-(6-chloropyridin-3-yl)methyl)ethane-1,2-diamine;

(2): A mixture of $N^1$-(6-chloropyridin-3-yl)methyl) ethane-1,2-diamine and 1,1-bis(methylthio)-2-nitroethylene is dissolved in ethanol, and refluxed for 4-8 hours to obtain nitromethylene compound.

(3): In the presence of acidic catalyst (such as hydrochloric acid, sulfuric acid, and heteropolyacids etc.), the nitromethylene compound is reacted with aldehyde to obtain the compound of formula (I).

In another embodiment, a compound of formula (II) can be synthesized by the following procedure:

(1): Proper amount of acetonitrile is added to a solution of aqueous ethylamine. 6-chloro-3-(chloromethyl) pyridine in acetonitrile is then added dropwise at 0° C. The reaction is monitored by TLC. After completion, the mixture, to which a large amount of water is added, is extracted by dichloromethane (DCM), dried, filtered and evaporated to remove the solvent and obtain N-(6-chloropyridinyl-3-methylene)-ethylamine as oil.

(2): A mixture of N-(6-chloropyridinyl-3-methylene)-ethylamine and 1,1-bis(methylthio)-2-nitroethylene is dissolved in ethanol and refluxed for 4-8 hours. After completion, the mixture is concentrated and purified by column chromatography to obtain the N-(6-chloropyridinyl-3-methylene)-N-ethyl-1-methylthio-2-nitrovinylidene amine.

(3): A mixture of methylamine alcohol and N-(6-chloropyridinyl-3-methylene)-N-ethyl-1-methylthio-2-nitrovinylidene amine is dissolved in ethanol and reacted in ice bath for 4-8 hours. After completion, the mixture is concentrated and purified by column chromatography to obtain N-(6-chloropyridinyl-3-methylene)-N-ethyl-N'-methyl-2-nitrovinylidene-diamine.

(4): In the presence of acidic catalyst (such as hydrochloric acid, sulfuric acid, and heteropolyacid etc.), N-(6-chloropyridinyl-3-methylene)-N-ethyl-N'-methyl-2-nitrovinylidene-diamine is reacted with aldehyde to obtain the compound of structure (II).

In another embodiment, a compound of formula (III) can be synthesized by the following procedure:

(1): To a mixture of 2-chloro-5-(2-nitromethylene-imidazolidin-1-yl-methyl)-pyridine, potassium carbonate and DMF, 1-1.5 mole eq. of iodomethane is added dropwise. The obtained mixture is reacted at 10-20° C. for 2-4 hrs. After completion, the mixture, to which water is added, is extracted by DCM and evaporated to obtain 2-chloro-5-(3-methyl-2-nitromethylene-imidazolidin-1-yl-methyl)-pyridine.

(2): In the presence of acidic catalyst (such as hydrochloric acid, sulfuric acid, and heteropolyacid etc.), 2-chloro-5-(3-methyl-2-nitromethylene-imidazolidin-1-yl-methyl)-pyridine is reacted with aldehyde to obtain the compound of formula (III).

Insecticidal Activity

The term "active compound in/of this invention" or "active substance in/of this invention" refers to the compound of the present invention, or the optical isomer, cis-trans isomer, or insecticidal acceptable salt thereof. The active compound in this invention shows significantly increased insecticidal activity and broadened insecticidal spectrum.

The term "insecticidal acceptable salt" refers to a salt in which the anion portion is known or acceptable when forming the insecticidal pharmaceutical acceptable salt. Preferably, the salt is water soluble. Suitable insecticidal acceptable salts of compounds of formula (I) and (II) include salts formed by inorganic acid, such as hydrochlorate, phosphate, sulfate, and nitrate, and salt formed by organic acid, such as acetate and benzoate.

The active substance of this invention can be used to control and kill general plant insects in agriculture and forestry, insects in the cereal in storage, and insects that harmful to public health. In this invention, the term "insecticide" refers to substances that can be used to prevent and control any of the above mentioned insects. The insects include but not limited to:

Coleoptera insects: *Sitophilus zeamai, Tribolium castaneum, Henosepilachna vigintioctomaculata, Henosepilachna sparsa, Agriotes fuscicollis, Anomala cupripes, Popillia quadriguttata, Monolepta hieroglyphica, Monochamus alternatus, Echinocnemus squameus, Basiprionota bisignata, Anoplophora chinensis, Apripona germari, Scolytus schevy, Agriotes fuscicollis.* Lepidoptera insects: *Lymantria dispar, Malacosoma neustria testacea, Diaphania perspectalis, Clania variegate, Cnidocampa flauescens, Dendrolimus punctatus, Orgyia gonostigma, Paranthrene tabaniformis, Spodoptera litura, Chilo suppressalis, Ostrinia nubilalis, Ephestia cautella, Adoxophyes orana, Laspyresia splendana, Agrotis fucosa, Galleria mellonella, Plutella xylostella, Phyllocnistis citrella, Mythimna separata.*

Homoptera insects: *Nephotettix cincticeps, Nilaparvata lugens, Pseudococcus comstocki, Unaspis yanonensis, Myzus persicae, Aphis gossydii, Lipaphis erysimi pseudobrassicae, Stephanitis nashi, Bemisia tabaci.*

Orthoptera insects: *Blattella germanica, Periplaneta americana, Gryllotalpa africana, Locus migratoria.*

Isoptera insects: *Solenopsis invicta, Coptotermes formosanus.*

Diptera insects: *Musca domestica, Aedes aegypti, Delia platura, Culex sp., Anopheles sinensis.*

The compounds of this invention have especially good effects to agriculture and plant insects having piercing-sucking or scratching mouthparts, such as aphid, leafhopper, plant hopper, thrips, and white fly.

Insecticidal Composition Comprising the Active Compounds of this Invention

The active compounds of this invention can be formulated into insecticidal composition via conventional method. The active compounds can be formulated into conventional formulations, such as solutions, emulsions, suspensions, powders, foams, pastes, granules, aerosols, natural and synthetic materials impregnated with the active compounds, microcapsules in polymers, coated complex for seed, preparations used with a combustion device (such as smoking cylindrantherae, smoking can and smoking plate), and ULV cold mist and warm mist preparations.

These formulations may be produced by a known method, for example, by mixing the active compounds with extenders, which are liquid, liquefied gaseous or solid diluents or carriers, optionally with surface-active agents, which is emulsifying agents and/or dispersing agents, and/or foam-forming agents. In the case of using water as an extender, organic solvents can also be used as auxiliary solvents.

It is generally proper to use liquid solvents as a diluent or carrier, wherein said liquid solvents can be for example: aromatic hydrocarbons, such as xylene, toluene and alkyl naphthalenes; chlorinated aromatic or chlorinated aliphatic hydrocarbons, such as chlorobenzenes, chloroethylenes and methylene chloride; aliphatic hydrocarbons, such as cyclohexane or paraffins, for example, mineral oil fractions; alcohols, such as butanol or glycol as well as their ethers and esters, ketones, such as acetone, methyl ethyl ketone, methyl isobutyl ketone or cyclohexanone; or polar solvents of unusual use, such as dimethylformamide and dimethylsulfoxide; as well as water. The term liquefied gaseous diluents or carriers refers to liquids which are gaseous at normal temperature and under normal pressure, for example, aerosol propellants, such as halogenated hydrocarbons, butane, propane, nitrogen and carbon dioxide.

The solid carrier can use ground natural minerals, such as kaolins, clays, talcs, quartzs, attapulgites, montmorillonites or kieselguhrs; ground synthetic minerals, such as high dispersed silicic acid, alumina and silicate. The solid carrier used for particles is crushed and fractionated natural rocks such as calcite, marble, pumice, sepiolite and dolomite, as well as synthetic granules of inorganic and organic coarse powder, and organic material such as sawdust, coconut shells, maize cobs and tobacco stalks and the like.

Nonionic and anionic emulsifiers may be used as emulsifying and/or foam-forming agents, such as polyoxyethylene-fatty acid esters, polyoxyethylene-fatty alcohol ethers (for example, alkylaryl polyglycol ethers, alkylsulfonates, alkylsulfates, arylsulfonates) as well as albumin hydrolysis products. Dispersing agents include, for example, lignin sulfite waste liquors and methyl cellulose.

Adhesives, such as carboxymethyl cellulose and natural or synthetic polymers (such as gum arabic, polyvinyl alcohol and polyvinyl acetate) in the form of powders, granules or emulsions, can be used in the formulations. Suitable colorants can be, such as, inorganic dyes (for example, iron oxide, cobalt oxide and Prussian Blue), and organic dyes (such as azo dyes or metal phthalocyanine dyes), and trace nutritional agents (such as the salts of iron, manganese, boron, copper, cobalt, aluminum and zinc).

The active compound of the present invention can be present as a mixture with other active compounds in a commercial formulation or a applicable form prepared from the commercial formulation. The other compound can be (but not limited to) insecticide, co-bait, bactericide, acaricide, nematocide, fungicide, growth controller and the like. The insecticide includes, for example, phosphates, carbamate, pyrethroids, chlorinated hydrocarbons, benzoylurea, nereistoxin, and materials produced by microbion (such as avilamycin).

Furthermore, the active compounds of the present invention can also be mixed with a synergist to from a mixture in a commercial formulation or an applicable form prepared from the commercial formulation. The synergist is used to enhance the activity of an active compound, as the compound itself is active and it is optional to use the synergist.

The formulation generally contains 0.001-99.99 wt % of active compound, preferably 0.01-99.9 wt %, more preferably 0.05-90 wt %, based on the total weight of the insecticidal composition.

The concentration of the active compound in the applicable form prepared from the commercial formulation can vary within a wide range. The concentration of active compound in the applicable formulation can be, for example, from 0.0000001 to 100% (g/v), preferably from 0.0001 to 1%.

EXAMPLES

The invention is further illustrated by the following examples. It should be appreciated that these examples are only intended to illustrate the invention, but not to limit the scope of the invention. For the experimental methods in the following examples, they are performed under routine conditions, or as instructed by the manufacturers, unless otherwise specified. The percentage and portion are calculated by weight while r.t. represents room temperature.

Example 1

Synthesis of 2-chloro-5-((2-(2-(furan-2-yl)-1-nitrovinyl)-4,5-dihydroimidazol-1-yl) -methyl) pyridine (Compound 1)

According to the methods disclosed in WO 2006056108A1 and WO2007101369A1, 2-chloro-5-(2-nitromethylene-imidazolidin-1-yl-methyl)-pyridine was prepared from 2-chloro-5-(chloromethyl)pyridine (0.03 mol) with a yield of 56%; $R_f$=0.46 (petroleum ether (PE): EtOAc=1:1); mp=156.9° C.-161.8° C.; GC MS(m/s): 220 (25), 126(100), 90(9).

Synthesis of 2-chloro-5-((2-(2-(furan-2-yl)-1-nitrovinyl)-4,5-dihydroimidazol-1-yl)-methyl) pyridine (Compound 1)

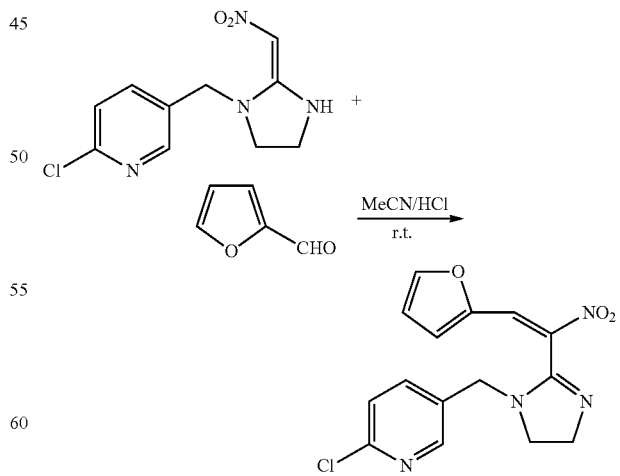

To a 50 ml round bottom flask, 1.27 g (0.005 mol) 2-chloro-5-(2-nitromethylene-imidazolidin-1-ylmethyl)-pyridine, 30 ml anhydrous acetonitrile, 0.576 g (0.006 mol) furaldehyde, and catalytic amount of concentrated HCl were added. The reaction was stirred at r.t. for about two hours to produce a large amount of solid. After the completion of the reaction, the solid was collected by filtration as a crude product. Pure final product (1.5 g) was obtained by recrystallization as yellow powder with 90% yield.

mp=200.4-201.6° C.; $^1$H NMR (400 Mz, DMSO-$d_6$): δ 8.74 (s, 1H), 8.23 (d, J=2.4 Hz, 1H), 8.20 (d, J=1.2 Hz, 1H), 7.68-7.71 (m, 2H), 7.49 (d, J=8.4 Hz, 1H), 6.92 (dd, $J_1$=1.6 Hz, $J_2$=3.6 Hz, 1H), 4.78 (d, J=15.6 Hz, 1H), 4.67 (d, J=15.6 Hz, 1H), 4.08-4.18 (m, 4H) ppm; $^{13}$C NMR (100 Mz, DMSO-$d_6$): δ 158.7, 153.2, 150.7, 150.3, 144.9, 140.3, 131.1, 129.7, 129.5, 126.2, 124.7, 115.6, 49.7, 46.9, 44.5 ppm; IR (KBr) 3127, 3106, 2973, 2803, 2608, 1633, 1607, 1581, 1499, 1309, 1021, 883, 790, cm$^-$; HRMS (ES+) calcd for $C_{15}H_{14}N_4O_3{}^{35}Cl$ (M+H)$^+$, 333.0754; found, 333.0761; calcd for $C_{15}H_{14}N_4O_3{}^{37}Cl$ (M+H)$^+$, 335.0725; found, 335.0766.

Example 2

Synthesis of 2-chloro-5-((2-(2-(furan-3-yl)-1-nitrovinyl)-4,5-dihydro-imidazol-1-yl)-methyl) pyridine (Compound 2)

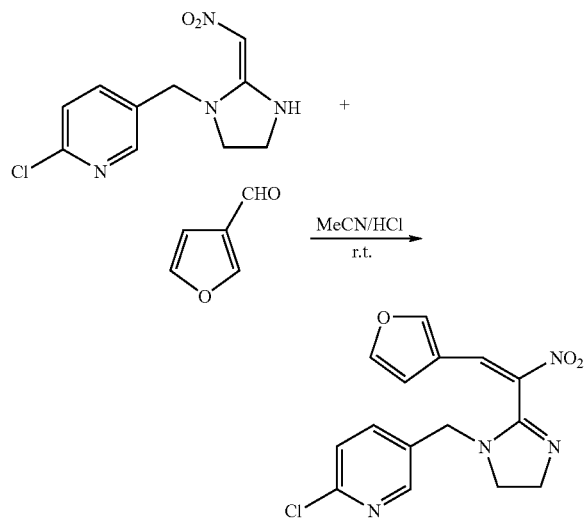

To a 50 ml round bottom flask, 1.27 g (0.005 mol) 2-chloro-5-(2-nitromethylene-imidazolidin-1-yl-methyl)-pyridine, 30 ml anhydrous acetonitrile, 0.576 g (0.006 mol) 3-furaldehyde, and catalytic amount of concentrated HCl were added. The reaction was stirred at r.t. for about two hours to produce a large amount of solid. After the completion of the reaction, the solid was collected by filtration as a crude product. Pure final product (0.862 g) was obtained by recrystallization as taupe powder with 51.9% yield.

mp=175.3-175.9° C.; $^1$H NMR (400 Mz, DMSO-$d_6$): δ 8.86 (s, 1H), 8.70 (s, 1H) 8.27 (d, J=2.4 Hz, 1H), 8.02 (s, 1H) 7.71 (dd, $J_1$=2.4 Hz, $J_2$=8.4 Hz, 1H), 7.52 (d, J=8.4 Hz, 1H), 6.61 (d, J=0.8 Hz, 1H), 4.75 (d, J=15.2 Hz, 1H), 4.68 (d, J=15.2 Hz, 1H), 4.05-4.25 (m, 4H) ppm; $^{13}$C NMR (100 Mz, DMSO-$d_6$): δ 157.9, 154.9, 150.8, 150.6, 148.92, 140.7, 137.8, 129.2, 128.9, 124.8, 116.8, 108.7, 49.7, 46.9, 44.6 ppm; HRMS (EI+) calcd for $C_{15}H_{13}N_4O_3{}^{35}Cl$ (M$^+$), 332.0676; found, 332.0676; calcd for $C_{15}H_{13}N_4O_3{}^{37}Cl$ (M$^+$), 334.0674; found, 334.0651.

Example 3

Synthesis of 2-chloro-5-((2-(1-nitro-2-(thiophen-2-yl)vinyl)-4,5-dihydro-imidazol-1-yl)-methyl)pyridine (Compound 16)

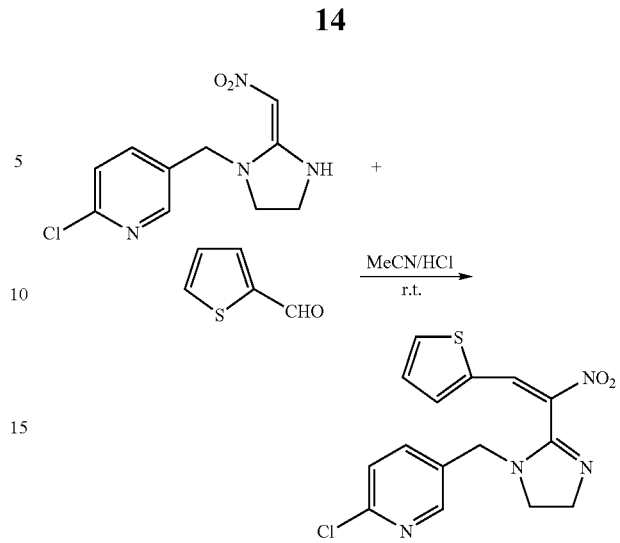

To a 50 ml round bottom flask, 1.27 g (0.005 mol) 2-chloro-5-(2-nitromethylene-imidazolidin-1-yl-methyl)-pyridine, 30 ml anhydrous acetonitrile, 0.672 g (0.006 mol) thiophene-1-formaldehyde, and catalytic amount of concentrated HCl were added. The reaction was stirred at r.t. for about 3 hr to produce a large amount of solid. After the completion of the reaction, the solid was collected by filtration as a crude product. Pure final product (1.253 g) was obtained by recrystallization as bright yellow powder with 72.1% yield.

mp=188.8-189.7° C.; $^1$H NMR (400 Mz, DMSO-$d_6$): δ 9.18 (s, 1H), 8.37 (d, J=4.8 Hz, 1H), 8.27 (d, J=1.6 Hz, 1H), 8.14(d, J=3.6 Hz, 1H), 7.71 (dd, $J_1$=2.0 Hz, $J_2$=8.4 Hz, 1H), 7.50 (d, J=8.4 Hz, 1H), 7.43 (d, J=4.4 Hz, 1H), 4.82(d, J=15.2 Hz, 1H), 4.68 (d, J=15.2 Hz, 1H), 4.15 (s, 4H) ppm; $^{13}$C NMR (100 Mz, DMSO-$d_6$): δ 157.8, 150.8, 150.6, 143.2, 140.6, 140.4, 139.3, 131.4, 130.6, 129.1, 127.2, 124.7 49.7, 46.9, 44.8 ppm; HRMS (EI+) calcd for $C_{15}H_{13}N_4O_2S{}^{35}Cl$ (M$^+$), 348.0448; found, 348.0446; calcd for $C_{15}H_{13}N_4O_2S{}^{37}Cl$ (M$^+$), 335.0418; found, 350.0431.

Example 4

Synthesis of 1-((2-chlorothiozol-5-yl)methyl)-2-(2-(furan-2-yl)-1-nitrovinyl)-4,5-dihydro-1H-imidazole (Compound 68)

According to the method of Example 1, 1-((2-chlorothiozol-5-yl)methyl)-2-(nitromethylene)-1-imidazolidine was obtained in a yield of 56% yield using 2-chloro-5-(chloromethyl)thiazole (0.03 mol) instead of 2-chloro-5-(chloromethyl) pyridine as a starting material. GC MS(m/s) 226 (24), 132(100), 77(9).

Synthesis of 1-((2-chlorothiozol-5-yl)methyl)-2-(2-(furan-2-yl)-1-nitro-vinyl)-4,5-dihydro-1H-imidazole

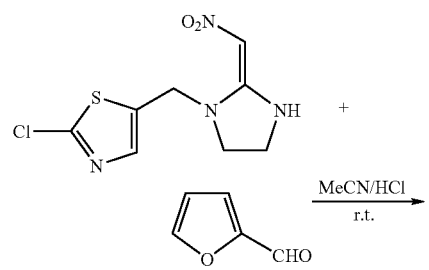

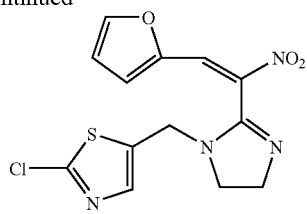

To a 50 ml round bottom flask, 1.30 g (0.005 mol) 1-((2-chlorothiozol-5-yl)methyl)-2-(nitromethylene)-1-imidazolidine, 30 ml anhydrous acetonitrile, 0.576 g (0.006 mol) furaldehyde, and catalytic amount of concentrated HCl were added. The reaction was stirred at r.t. for about 3 hr to produce a large amount of solid. After the completion of the reaction, the solid was collected by filtration as a crude product. Pure final product (0.579 g) was obtained by recrystallization as yellow powder with 33.3% yield.

mp=198.2-198.7° C.; 1H NMR (400 Mz, DMSO-$d_6$): δ 8.75 (s, 1H), 8.19 (s, 1H), 7.71 (d, J=3.2 Hz, 1H), 7.61 (s, 1H), 6.92-6.93 (m, 1H), 4.97 (s, 2H), 4.13 (s, 4H) ppm; $^{13}$C NMR (100 Mz, DMSO-$d_6$): δ 158.4, 153.2, 152.2, 145.0, 142.9, 133.6, 131.2, 129.7, 126.0, 115.7, 49.3, 44.6, 42.3 ppm; HRMS (EI+) calcd for $C_{13}H_{11}N_4O_3S^{35}Cl$ (M$^+$), 338.0240; found, 338.0240. calcd for $C_{13}H_{11}N_4O_3S^{37}Cl$ (M$^+$), 340.0211; found, 340.0213.

Example 5

Synthesis of 1-((2-chlorothiozol-5-yl)-2-(1-nitro-2-(5-nitrofuran-2-yl)vinyl)-4,5-dihydro-1H-imidazole (Compound 70)

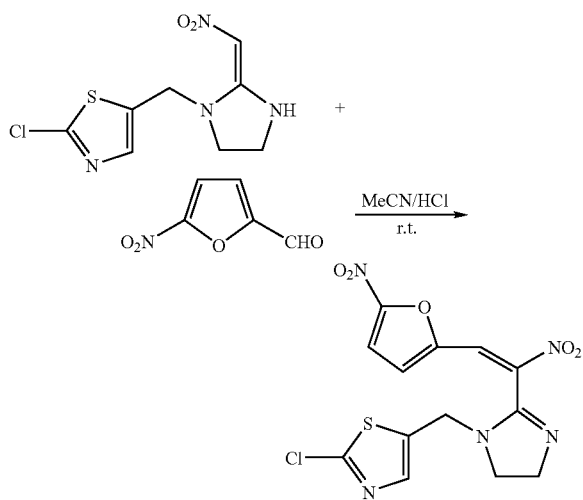

To a 50 ml round bottom flask, 1.30 g (0.005 mol) 1-((2-chlorothiozol-5-yl)methyl)-2-(nitromethylene)-1-imidazolidine, 30 ml anhydrous acetonitrile, 0.576 g (0.006 mol) furfuraldehyde, and catalytic amount of concentrated HCl were added. The reaction was stirred at r.t. for about 3 hr to produce a large amount of solid. After the completion of the reaction, the solid was collected by filtration as a crude product. Pure final product (0.970 g) was obtained by recrystallization as yellow powder with 53.3% yield.

mp=189.2-190.7° C.; 1H NMR (400 Mz, DMSO-$d_6$): δ 8.71 (s, 1H), 7.70 (d, J=3.2 Hz, 1H), 7.64 (s, 1H), 6.91-6.93 (m, 1H), 4.95 (s, 2H), 4.13 (s, 4 H) ppm; $^{13}$C NMR (100 Mz, DMSO-$d_6$): δ 157.4, 153.1, 152.2, 146.0, 143.9, 133.8, 131.9, 129.0, 126.7, 115.7, 49.5, 44.6, 42.6 ppm; HRMS (EI+) calcd for $C_{13}H_{10}N_5O_5S^{35}Cl$ (M$^+$), 383.0091; found, 383.0087. calcd for $C_{13}H_{10}N_5O_5S^{37}Cl$ (M$^+$), 385.0062; found, 385.050.

Example 6

Synthesis of ((6-chloropyridin-3-yl)methyl)-2-(2-(furan-2-yl)-1-nitrovinyl)-1,4,5,6-tetrahydro-pyrimidine (Compound 46)

According to the methods disclosed in WO 2006056108A1 and WO2007101369A1, 1-(6-chloro-3-methylpyridinyl)-2-nitromethylene hexahydro-pyrimidine was produced in a yield of 56% started from parachloropyridine (2.42 g, 0.015 mol). Rf=0.19 (EtOH/DCM=1:1); mp=175.7-182.6° C. GC MS (m/s) 225(100), 196(9), 154(10), 139(11), 126(31), 113(10), 99(31).

Synthesis of 1-((6-chloropyridin-3-yl)methyl)-2-(2-(furan-2-yl)-1-nitrovinyl)-1,4,5,6-tetrahydropyrimidine

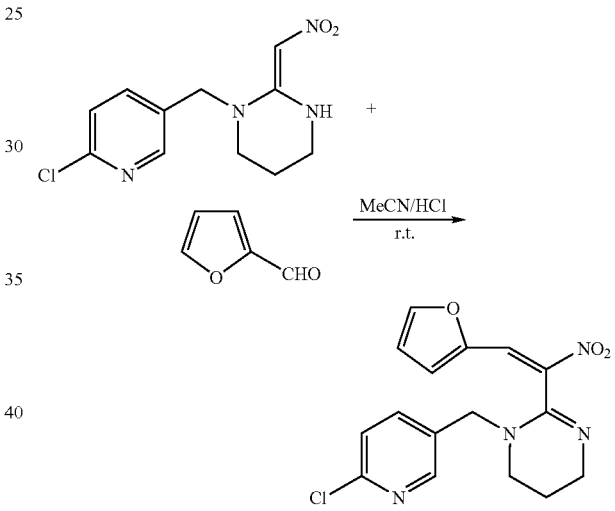

The compound was prepared according to the method disclosed in Example 1 with 51% yield stared from 1-(6-chloropyridin-3-ylmethyl)-2-nitromethylene-hexahydropyrimidine.

mp=162.5-163.9° C.; $^1$H NMR (400 Mz, DMSO-$d_6$): δ 8.72 (s, 1H), 8.20 (d, J=2.4 Hz, 1H), 8.18 (d, J=1.2 Hz, 1H), 7.63-7.70 (m, 2H), 7.49 (d, J=8.4 Hz, 1H), 6.82 (dd, $J_1$=1.6 Hz, $J_2$=3.6 Hz, 1H), 4.75 (d, J=15.6 Hz, 1H), 4.63 (d, J=15.6 Hz, 1H), 4.08-4.18 (m, 4H), 3.51-3.56(m, 1H) ppm; $^{13}$C NMR (100 Mz, DMSO-$d_6$): δ 158.7, 153.2, 150.7, 150.3, 144.9, 140.3, 131.1, 129.7, 129.5, 126.2, 124.7, 115.6, 49.7, 46.9, 44.5, 39.8 ppm; HRMS (EI+) calcd for $C_{16}H_{15}N_4O_3^{35}Cl$ (M+H)$^+$, 346.0833; found, 346.0877. calcd for $C_{16}H_{15}N_4O_3^{37}Cl$ (M+H)$^+$, 348.0803; found, 348.0897.

Example 7

Synthesis of N-((6-chloropyridin-3-yl)methyl)-N-ethyl-3-(furan-2-yl)-N'-methyl-2-nitro acrylamidine (Compound 151)

(1): Synthesis of N-(6-chloropyridin-3-yl-methene)ethylamine

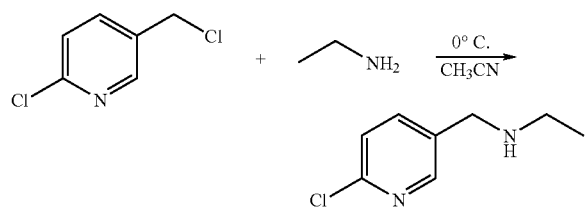

To a three necked 300 mL round bottom flask which was equipped with a pressure-equalizing dropping funnel and a thermometer, 65-70% aqueous ethylamine solution (70 g, 1 mol), and acetonitrile (50 mL) were added. The solution was stirred in ice bath for 15 min to keep the temperature at about 0° C. Then, 6-chloro-3-(chloromethyl)pyridine (16.10 g, 0.10 mol) in 25 ml acetonitrile was added by pressure-equalizing dropping funnel in 3.5 hr with a speed of 3 drop/min. After completion, the reaction was diluted with water and extracted with DCM. The organic phase was collected to obtain 14 g N-(6-chloropyridin-3-yl-methylene)ethylamine as oil with 70% yield. GC-MS: m/z (%)=170 ([M]+, 20), 155 (80), 126 (100), 114 (10), 90 (12).

(2): Synthesis of N-(6-chloropyridin-3-yl)methylene)-N-ethyl-1-(methylthio)-2-nitrovinylidene amine

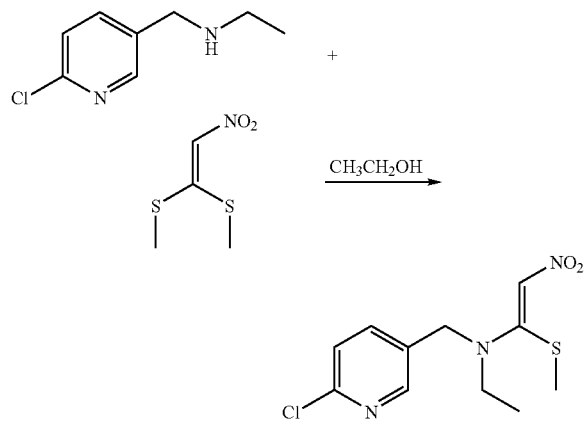

To a 100 ml three necked round bottom flask, N-(6-chloropyridin-3-yl-methylene)ethylamine (17.0 g, 0.1 mol), 1,1-bis(methylthio)-2-nitroethene (15.0 g, 0.09 mol), anhydrous ethanol (50 mL) were added. The mixture was refluxed until full convention and cooled to r.t., The reaction was concentrated with reduced pressure to obtain a crude product as dense liquid, which was purified by column chromatography to yield 5.3 g N-(6-chloropyridin-3-yl-methylene)-N-ethyl-1-(methylthio)-2-nitrovinylidene amine in 18.5% yield.

GC-MS: m/z (%)=242 ([M]+-46, 53), 227 (15), 213 (100), 169 (45), 155 (28), 141 (29), 126 (91), 90 (12).

(3): Synthesis of N-(6-chloropyridin-3-yl-methylene)-N-ethyl-N-methyl-2-nitrovinylidene-diamine

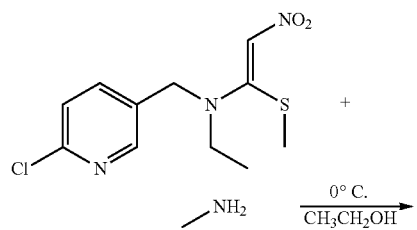

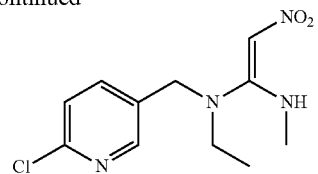

To a 100 ml round bottom flask, N-(6-chloropyridin-3-yl-methylene)-N-ethyl-1-(methylthio)-2-nitrovinylidene amine (5.0 g, 0.017 mol), methylamine alcohol solution (1.8 g, 0.017 mol methylamine), anhydrous ethanol (30 mL) were added. The mixture was stirred in ice bath to lower the temperature to 0° C. and keep such a temperature till the end of the reaction. The solution was concentrated by rotary evaporation to obtain a slurry. The slurry was solved in DCM and purified by column chromatography using DCM/EtOH=25:1 as eluent on a column filled with silicon gel. 0.9 g N-(6-chloropyridin-3-yl-methylene)-N-ethyl-N'-methyl-2-nitrovinylidene diamine was obtained with 19.1% yield. Rf=0.23 (TLC: DCM/Acetone=5:1,); mp=78-80° C.; GC-MS: m/z (%)=236 ([M]+-34, 32), 207 (49), 169 (52), 126 (49), 110 (20), 90 (16), 67 (100), 16.65.

(4): Synthesis of N-((6-chloropyridin-3-yl)methyl)-N-ethyl-3-(furan-2-yl)-N'-methyl-2-nitroacrylamidine

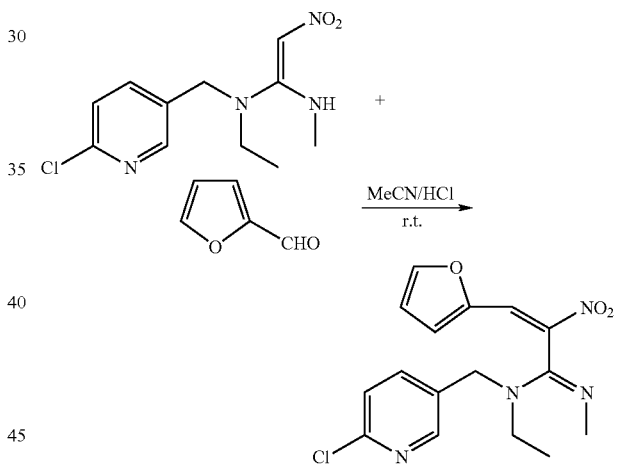

To a 50 ml round bottom flask, 1.35 g (0.005 mol) N-((6-chloropyridin-3-yl-methylene)-N-ethyl-N'-methyl-2-nitrovinylidene diamine, 30 ml anhydrate acetonitrile, 0.576 g (0.006 mol) furaldehyde and catalytic amount of concentrated HCl were added. The reaction was stirred at r.t. for about 6 hr to produce a large amount of solid. After the completion of the reaction, the solid was collected by filtration as a crude product. Pure final product (0.986 g) was obtained by recrystallization as yellow powder with 70.1% yield.

mp=155.3-155.7° C.; 1H NMR (400 Mz, DMSO-$d_6$): δ 8.81 (s, 1H), 8.72 (s, 1H), 8.27 (d, J=2.4 Hz, 1H), 8.13 (s, 1H), 7.75 (dd, $J_1$=2.4 Hz, $J_2$=8.4 Hz, 1H), 7.58 (d, J=8.4 Hz, 1H), 6.66 (d, J=0.8 Hz, 1H), 4.44-4.50 (m, 2H), 2.96-3.26 (m, 2H), 2.86 (s, 3H), 1.16-1.26 (m, 3H) ppm; $^{13}$C NMR (100 Mz, DMSO-d6): δ 158.5, 154.4, 151.6, 150.8, 148.1, 139.3, 137.1, 129.6, 128.6, 125.1, 117.8, 107.8, 49.8, 46.9, 40.6, 21.9 ppm; HRMS (EI+) calcd for $C_{16}H_{17}N_4O_3{}^{35}Cl$ ($M^+$), 348.0989; found, 348.0996. calcd for $C_{16}H_{17}N_4O_3{}^{37}Cl$ ($M^+$), 350.0960; found, 350.0971.

Example 8

Synthesis of N-((6-chloropyridin-3-yl)methyl)-N-ethyl-N'-methyl-2-nitro-3-(1H-pyrrol-2-yl) acrylamidine (Compound 160)

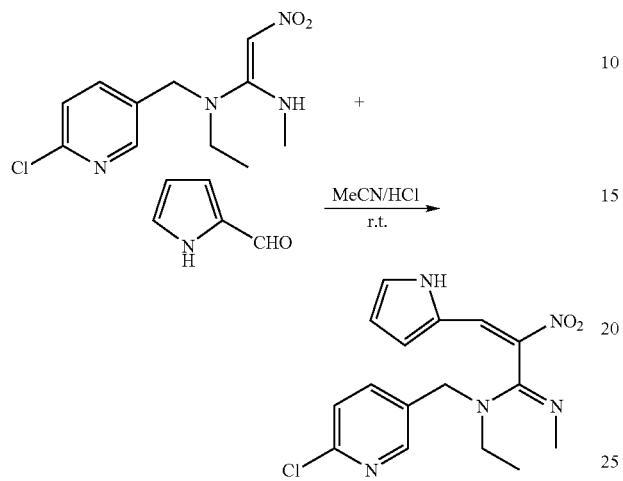

The synthesis was carried out according to Example 1, except that the starting material furaldehyde was replaced with pyrrole-2-formaldehyde. The yield was 69%.

mp=165.3-166.7° C.; $^1$H NMR (400 Mz, DMSO-d$_6$): δ 8.87 (s, 1H), 8.76 (s, 1H), 8.37 (d, J=2.4 Hz, 1H), 8.18 (s, 1H), 7.76 (dd, J$_1$=2.4 Hz, J$_2$=8.4 Hz, 1H), 7.58 (d, J=8.4 Hz, 1H), 6.60 (d, J=0.8 Hz, 1H), 6.06 (s, 1H), 4.50-4.58 (m, 2H), 2.86-3.21 (m, 2H), 2.78 (s, 3H), 1.12-1.21 (m, 3H) ppm; $^{13}$C NMR (100 Mz, DMSO-d6): δ 158.0, 154.8, 150.6, 150.1, 148.5, 140.3, 137.1, 129.7, 128.6, 125.8, 117.8, 108.8, 49.7, 46.9, 40.6, 21.1 ppm; HRMS (EI+) calcd for C$_{16}$H$_{18}$N$_5$O$_2$$^{35}$Cl (M$^+$), 347.1149; found, 347.1166. calcd for C$_{16}$H$_{18}$N$_5$O$_2$$^{37}$Cl (M$^+$), 349.1120; found, 349.1138.

Example 9

Synthesis of 2-(2-(furan-2-yl)-1-nitrovinyl)-1-((tetrahydrofuran-3-yl)methyl)-4,5-dihydro-1H-imidazole (Compound 91)

(1): N'-((tetrahydrofuran-3-yl)methyl)ethane-1,2-diamine

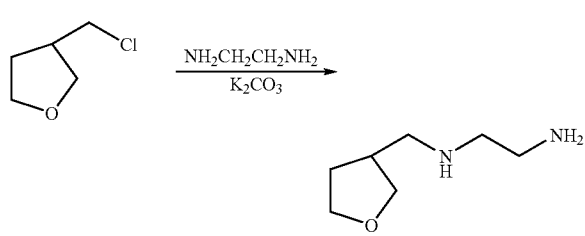

A solution of 3-(chloromethyl)tetrahydrofuran (0.2 mol), K$_2$CO$_3$ (0.2 mol) and ethylenediamine (0.2 mol) in 200 mL ethanol was added into a round bottom flask and refluxed for 24 hrs. The mixture was then concentrated to obtain N-((tetrahydrofuran-3-yl)methyl) ethane-1,2-diamine as yellow oil with 77% yield was obtained. GC MS(m/s) 144 (67), 99(100).

(2): 1-((tetrahydrofuran-3-yl)methyl)-2-(nitromethylene)-1-imidazolidine

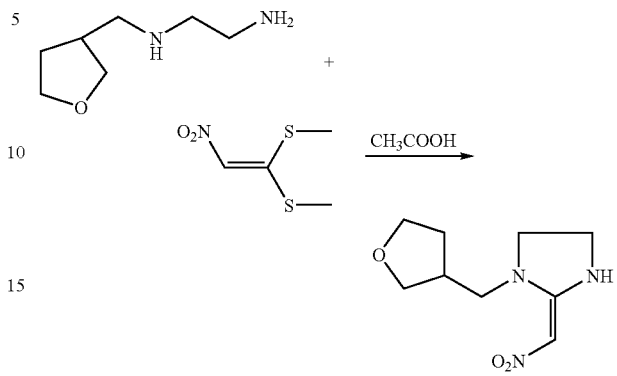

A solution of 1,1-bis(methylthio)-2-nitroethylene (2.5 g, 0.0178 mol) and N'-((tetrahydrofuran-3-yl)methyl)ethane-1,2-diamine (2.56 g, 0.0178 mol) in 50 ml ethanol was refluxed at 80-90° C. for 8 hrs, and then cooled to r.t. The resulted solid was concentrated, filtrated, and dried to obtain light yellow powder product with 81% yield. GC MS (m/s) 177(29), 99(100), 56(9).

(3): 2-(2-(furan-2-yl)-1-nitrovinyl)-1-((tetrahydrofuran-3-yl)methyl)-4,5-dihydro-1H-imidazole

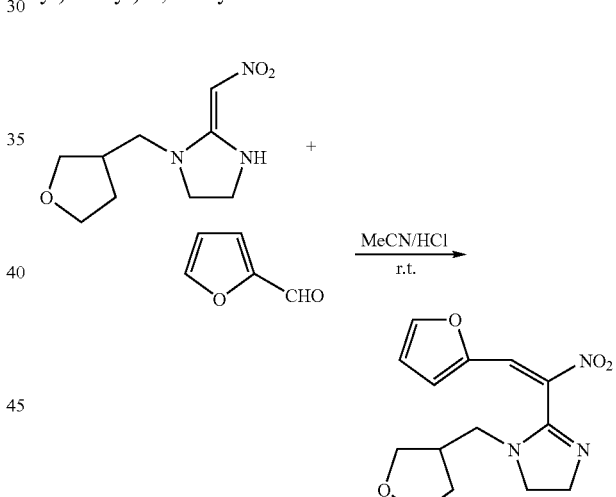

To a 50 ml round bottom flask, 1.065 g (0.005 mol) 1-((tetrahydrofuran-3-yl)methyl)-2-(nitromethylene)-imidazoline, 30 ml anhydrous acetonitrile, 0.576 g (0.006 mol) furaldehyde and catalytic amount of concentrated HCl were added. The reaction was stirred at r.t. for 8 hrs to produce a large amount of solid. After the completion of the reaction, the solid was collected by filtration to obtain a crude product. Pure final product (0.832 g) was obtained by recrystallization as yellow powder with 75.1% yield.

mp=115.3-116.9° C.; $^1$H NMR (400 Mz, DMSO-d$_6$): δ 8.86 (s, 1H), 8.72 (s, 1H), 8.12 (s, 1H), 6.61 (d, J=0.8 Hz, 1H), 4.18 (d, J=3.2 Hz, 2H), 4.05-4.25 (m, 4H), 3.85-3.96 (m, 4H), 2.25 (m, 1H), 1.63 (m, 2H) ppm; $^{13}$C NMR (100 Mz, DMSO-d$_6$): δ 158.0, 152.9, 148.7, 135.8, 129.7, 124.8, 116.8, 80.6, 78.5, 49.7, 46.9, 44.6, 36.8, 33.9 ppm; HRMS (EI+) calcd for C$_{14}$H$_{17}$N$_3$O$_4$(M$^+$), 291.1219; found, 291.1198.

Example 10

Synthesis of the Onium Salt of Compound 244
(1): Synthesis of 2-chloro-5-(3-methyl-2-nitromethylene-imidazolidin-1-ylmethyl)-pyridine

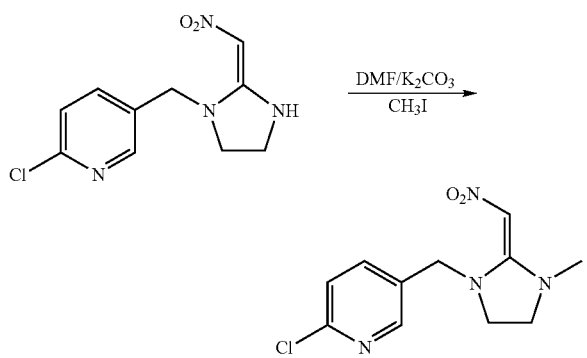

To a round bottom flask, 2-chloro-5-(2-nitromethylene-imidazolidin-1-yl) methyl)-pyridine (2.54 g, 0.01 mol), $K_2CO_3$ (2.05 g, 0.015 mol), and 20 ml dry DMF were added. Iodomethane (1.55, 1.1 mol) was added dropwise into the stirred mixture. The reaction was stirred for another 2 hrs, and then supplied with 50 ml water, extracted by DCM (5×20 ml). The organic phase was combined and concentrated to obtain 2.1 g product as white powder with 79% yield.

(2): Synthesis of the Onium Salt

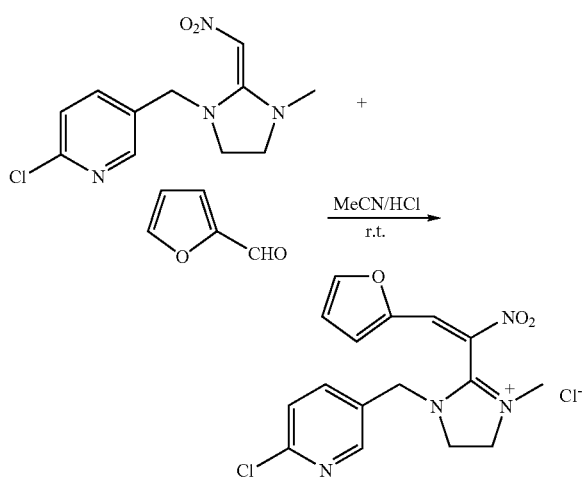

To a 50 ml round bottom flask, 1.33 g (0.005 mol) 2-chloro-5-(3-methyl-2-nitromethylene-imidazolidin-1-yl-methyl) pyridine, 30 ml anhydrous acetonitrile, 0.576 g (0.006 mol) furaldehyde and catalytic amount of concentrated HCl were added. The reaction was stirred at r.t. for 5 hrs to obtain a large amount of solid. After the completion of the reaction, the solid was collected by filtration as a crude product. Pure final product (1.300 g) was obtained by recrystallization as yellow powder with 77% yield.

mp=211.8-213.0° C.; $^1H$ NMR (400 Mz, DMSO-$d_6$): δ 8.73 (s, 1H), 8.21 (d, J=2.4 Hz, 1H), 8.18 (d, J=1.2 Hz, 1H), 7.66-7.72 (m, 2H), 7.50 (d, J=8.4 Hz, 1H), 6.88 (dd, $J_1$=1.6 Hz, $J_2$=3.6 Hz, 1H), 4.77 (d, J=15.6 Hz, 1H), 4.65 (d, J=15.6 Hz, 1H), 4.10-4.18 (m, 4H), 3,21(s, 3H) ppm; HRMS (ES+) calcd for $C_{16}H_{16}N_4O_3{}^{35}Cl$ (M+H)$^+$, 347.0911; found, 347.0771. calcd for $Cl_{16}H_{16}N_4O_3{}^{37}Cl$ (M+H)$^+$, 349.0881; found, 335.0776.

Example 11

Insecticidal Activity Tests of the Compounds of the Present Invention (1): Insecticidal Activities to Aphids Aphis (*Aphis craccivoral*), which belongs to Homoptera and has a piercing-sucking mouthpart, is a common insect for agricultural plant. *Aphis craccivoral* was tested by immersion method.

Procedure: exactly weighed various samples were independently added to N,N-dimethylformamide to form 10 g/L stock solutions. The stock solutions were diluted with 0.2 mL/L aqueous Triton X-100 solution to a concentration of 500 ppm. After stably sucking on bean sprout, the wingless adult aphis together with bean sprout were dipped into 500 ppm dilution, taken out after 5 seconds, and the excess dilution was sucked off with bibulous paper. The treated wingless adult aphis was incubated in clean vessel at a constant temperature of 23° C. Each concentration was repeated for 3 times and the control group was treated with 0.2mL/L aqueous Triton X-100 solution. The number of killed aphis was counted after 24 hours and the mortality was to calculated according to the following formula:

Mortality (%)=(the number of the survival aphis in control group–the number of the survival aphis in the treatment group)/the number of the survival aphis in control group× 100%

The results were shown in Tables 1-3 below.

(2): Insecticidal Activities to Plant hopper

Plant hopper (*Nilaparvata lugens*), which belongs to Homoptera and has a piercing-sucking mouthpart, is a common insect for agricultural plant. *Nilaparvata lugens* was tested by spraying method.

Procedure: the test compound was exactly formulated with acetone to form solutions having concentrations of 500, 250, 100, 50, 25, 12.5, 6.25, 3.13, 1.57 and 0.79 ppm, respectively. Aqueous acetone solution was used as control. Each treatment was repeated for 3 tumblers (3 times). Two ml of solution was sprayed uniformly to each tumbler with a mini manual sprayer. 10 insects were introduced to every basin 6 hours before spraying. Three series of experiments were conducted. The number of killed insects was counted after 24 hours to calculate the mortality according to the above mentioned formula. The results were shown in Tables 1-3 bellow.

(3): Insecticidal Activities to Armyworm

Armyworm (*Pseudaletia separate Walker*) was tested by the way of leaf dipping and feeding. The test compound was exactly formulated with acetone into solutions having concentrations of 500, 250, 100, 50, 25, 12.5, 6.25, 3.13 and 1.57 ppm, respectively. Aqueous acetone solution was used as control. Fresh maize leaves were immersed in the solution for 3 seconds, dried at room temperature, and fed to the tested insects. Each treatment was tested with 10 insects and repeated for 3 tumblers (3 times). The number of killed insects was counted after 24 hours to calculate the mortality according to the above mentioned formula. The results were shown in Tables 1-3 bellow.

(4): Insecticidal Activities to Diamondback Moth

Diamondback moth (*Plutella xylostella*) was tested by the way of feeding dippedleaves. Fresh cabbage leaves were immersed in above mentioned solution for 3 seconds, dried at room temperature, and fed to the tested insects. Each treatment was tested with 10 insects and repeated for 3 tumblers (3 times), while water was used as control. The number of killed insects was counted after 24 hours to calculate the mortality according to the above mentioned formula. The results were shown in Tables 1-3 bellow.

TABLE 1

Insecticidal activities of compounds (I)

$$\text{(I)}$$

Structure (I): 
$$R_1-CH(R_5)-N(\text{ring}(CH_2)_n)-C(=N)-C(Y)=C(R_2)-Z$$

| Compd. | R₁ | R₂ | Z | Y | R₅ | n | *Aphis craccivoral* Mortality (%) 500 ppm | *Nilaparvata lugens* Mortality (%) 500 ppm | *Pseudaletia separate* Walker Mortality (%) 500 ppm | *Plutella xylostella* Mortality (%) 500 ppm |
|---|---|---|---|---|---|---|---|---|---|---|
| 1 | 6-chloropyridin-3-yl | H | furan-2-yl (5-methyl) | NO₂ | H | 0 | 100 | 100 | 100 | 100 |
| 2 | 6-chloropyridin-3-yl | H | 3-methylfuran-yl | NO₂ | H | 0 | 100 | 100 | 100 | 100 |
| 3 | 6-chloropyridin-3-yl | H | 5-methyl-2-nitrofuran-yl | NO₂ | H | 0 | 100 | 100 | 100 | 100 |
| 4 | 6-chloropyridin-3-yl | H | 5-chloro-2-methylfuran-yl | NO₂ | H | 0 | 100 | 100 | 100 | 100 |
| 5 | 6-chloropyridin-3-yl | H | 5-bromo-2-methylfuran-yl | NO₂ | H | 0 | 100 | 100 | 100 | 100 |
| 6 | 6-chloropyridin-3-yl | H | 4-chloro-2-methylfuran-yl | NO₂ | H | 0 | 100 | 100 | 100 | 100 |
| 7 | 6-chloropyridin-3-yl | H | 4-bromo-2-methylfuran-yl | NO₂ | H | 0 | 100 | 100 | 100 | 100 |
| 8 | 6-chloropyridin-3-yl | H | 4,5-dichloro-2-methylfuran-yl | NO₂ | H | 0 | 100 | 100 | 100 | 100 |
| 9 | 6-chloropyridin-3-yl | H | 3,5-dichloro-2-methylfuran-yl | NO₂ | H | 0 | 100 | 100 | 100 | 100 |

TABLE 1-continued
Insecticidal activities of compounds (I)
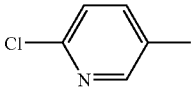
| | | | | | | | Insecticidal activities | | | |
| | | | | | | | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
| Compd. | $R_1$ | $R_2$ | Z | Y | $R_5$ | n | | | | |
|---|---|---|---|---|---|---|---|---|---|---|
| 10 | 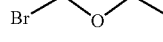 | H | 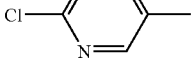 | $NO_2$ | H | 0 | 100 | 100 | 100 | 100 |
| 11 | 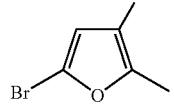 | H | 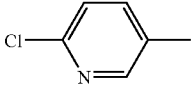 | $NO_2$ | H | 0 | 100 | 100 | 100 | 100 |
| 12 | 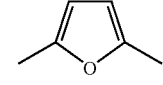 | H | 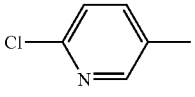 | $NO_2$ | H | 0 | 100 | 100 | 100 | 100 |
| 13 | 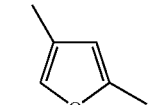 | H | 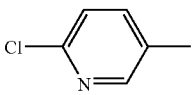 | $NO_2$ | H | 0 | 100 | 100 | 100 | 100 |
| 14 | 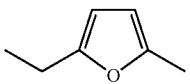 | H | 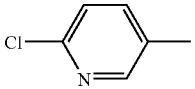 | $NO_2$ | H | 0 | 100 | 100 | 100 | 100 |
| 15 | 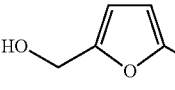 | H | 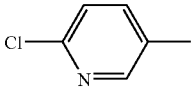 | $NO_2$ | H | 0 | 100 | 100 | 100 | 100 |
| 16 | 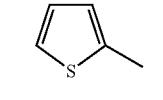 | H | 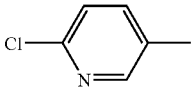 | $NO_2$ | H | 0 | 100 | 100 | 100 | 100 |
| 17 | 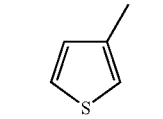 | H | 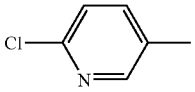 | $NO_2$ | H | 0 | 100 | 100 | 100 | 100 |
| 18 | 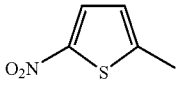 | H | | $NO_2$ | H | 0 | 100 | 100 | 100 | 100 |

TABLE 1-continued

Insecticidal activities of compounds (I)

(I)

| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 19 | 2-Cl-pyridin-5-yl | H | 5-Cl-thiophen-2-yl | NO₂ | H | 0 | 100 | 100 | 100 | 100 |
| 20 | 2-Cl-pyridin-5-yl | H | 5-Br-thiophen-2-yl | NO₂ | H | 0 | 100 | 100 | 100 | 100 |
| 21 | 2-Cl-pyridin-5-yl | H | 4-Cl-thiophen-2-yl (5-Me) | NO₂ | H | 0 | 100 | 100 | 100 | 100 |
| 22 | 2-Cl-pyridin-5-yl | H | 4-Br-thiophen-2-yl (5-Me) | NO₂ | H | 0 | 100 | 100 | 100 | 100 |
| 23 | 2-Cl-pyridin-5-yl | H | 4,5-diCl-thiophen-2-yl | NO₂ | H | 0 | 100 | 100 | 100 | 100 |
| 24 | 2-Cl-pyridin-5-yl | H | 3,5-diCl-thiophen-2-yl | NO₂ | H | 0 | 100 | 100 | 100 | 100 |
| 25 | 2-Cl-pyridin-5-yl | H | 4,5-diBr-thiophen-2-yl | NO₂ | H | 0 | 100 | 100 | 100 | 100 |
| 26 | 2-Cl-pyridin-5-yl | H | 3,5-diBr-thiophen-2-yl | NO₂ | H | 0 | 100 | 100 | 100 | 100 |
| 27 | 2-Cl-pyridin-5-yl | H | 5-Me-thiophen-2-yl | NO₂ | H | 0 | 100 | 100 | 100 | 100 |

TABLE 1-continued

Insecticidal activities of compounds (I)

Structure (I):

$$\begin{array}{c} R_2 \\ Z-C=C-Y \\ | \quad | \\ R_5 \quad C \\ | \quad / \backslash \\ R_1-CH-N \quad N \\ \quad \backslash \quad / \\ \quad (CH_2)_n \end{array}$$

| Compd. | $R_1$ | $R_2$ | Z | Y | $R_5$ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 28 | 6-chloropyridin-3-yl | H | 2,4-dimethylthien-5-yl | NO$_2$ | H | 0 | 100 | 100 | 100 | 100 |
| 29 | 6-chloropyridin-3-yl | H | 2-ethyl-5-methylthien-yl | NO$_2$ | H | 0 | 100 | 100 | 100 | 100 |
| 30 | 6-chloropyridin-3-yl | H | 5-(hydroxymethyl)-2-methylthien-yl | NO$_2$ | H | 0 | 100 | 100 | 100 | 100 |
| 31 | 6-chloropyridin-3-yl | H | 2-methyl-1H-pyrrol-5-yl | NO$_2$ | H | 0 | 100 | 100 | 100 | 100 |
| 32 | 6-chloropyridin-3-yl | H | 1,2-dimethyl-pyrrol-5-yl | NO$_2$ | H | 0 | 100 | 100 | 100 | 100 |
| 33 | 6-chloropyridin-3-yl | H | oxazol-5-yl-methyl | NO$_2$ | H | 0 | 100 | 100 | 100 | 100 |
| 34 | 6-chloropyridin-3-yl | H | thiazol-5-yl-methyl | NO$_2$ | H | 0 | 100 | 100 | 100 | 100 |
| 35 | 6-chloropyridin-3-yl | H | 2-chlorothiazol-5-yl-methyl | NO$_2$ | H | 0 | 100 | 100 | 100 | 100 |
| 36 | 6-chloropyridin-3-yl | H | 1H-imidazol-5-yl-methyl | NO$_2$ | H | 0 | 98 | 89 | 100 | 100 |

TABLE 1-continued

Insecticidal activities of compounds (I)

| Compd. | R$_1$ | R$_2$ | Z | Y | R$_5$ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 37 | 2-Cl-pyridin-5-yl | H | pyridin-2-yl | NO$_2$ | H | 0 | 34 | 56 | 57 | 50 |
| 38 | 2-Cl-pyridin-5-yl | H | pyridin-3-yl | NO$_2$ | H | 0 | 97 | 100 | 95 | 87 |
| 39 | 2-Cl-pyridin-5-yl | H | pyridin-4-yl | NO$_2$ | H | 0 | 24 | 35 | 35 | 21 |
| 40 | 2-Cl-pyridin-5-yl | H | 2-Cl-pyridin-5-yl | NO$_2$ | H | 0 | 45 | 44 | 67 | 56 |
| 41 | 2-Cl-pyridin-5-yl | H | 2-F-pyridin-5-yl | NO$_2$ | H | 0 | 89 | 87 | 100 | 100 |
| 42 | 2-Cl-pyridin-5-yl | H | 2-CH$_3$-pyridin-5-yl | NO$_2$ | H | 0 | 45 | 36 | 87 | 90. |
| 43 | 2-Cl-pyridin-5-yl | H | 1H-indol-2-yl | NO$_2$ | H | 0 | 76 | 90 | 95 | 100 |
| 44 | 2-Cl-pyridin-5-yl | H | phenyl | NO$_2$ | H | 0 | 67 | 92 | 97 | 100 |
| 45 | 2-Cl-pyridin-5-yl | H | 2-OH-phenyl | NO$_2$ | H | 0 | 56 | 76 | 89 | 23 |

TABLE 1-continued

Insecticidal activities of compounds (I)

(I)

| Compd. | $R_1$ | $R_2$ | Z | Y | $R_5$ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 46 | 6-Cl-pyridin-3-yl | H | 2-methylfuran-5-yl | $NO_2$ | H | 1 | 100 | 100 | 100 | 100 |
| 47 | 6-Cl-pyridin-3-yl | H | 3-methylfuran-4-yl | $NO_2$ | H | 1 | 100 | 100 | 100 | 100 |
| 48 | 6-Cl-pyridin-3-yl | H | 2-nitro-5-methylfuran | $NO_2$ | H | 1 | 100 | 100 | 100 | 100 |
| 49 | 6-Cl-pyridin-3-yl | H | 2-Cl-5-methylfuran | $NO_2$ | H | 1 | 100 | 100 | 100 | 100 |
| 50 | 6-Cl-pyridin-3-yl | H | 2-Br-5-methylfuran | $NO_2$ | H | 1 | 100 | 100 | 100 | 100 |
| 51 | 6-Cl-pyridin-3-yl | H | 3-Cl-5-methylfuran | $NO_2$ | H | 1 | 100 | 100 | 100 | 100 |
| 52 | 6-Cl-pyridin-3-yl | H | 3-Br-5-methylfuran | $NO_2$ | H | 1 | 100 | 100 | 100 | 100 |
| 53 | 6-Cl-pyridin-3-yl | H | 2,3-diCl-5-methylfuran | $NO_2$ | H | 1 | 100 | 100 | 100 | 100 |
| 54 | 6-Cl-pyridin-3-yl | H | 2,4-diCl-5-methylfuran | $NO_2$ | H | 1 | 100 | 100 | 100 | 100 |

TABLE 1-continued
Insecticidal activities of compounds (I)
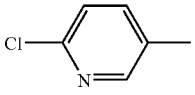
| Compd. | R$_1$ | R$_2$ | Z | Y | R$_5$ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 55 | 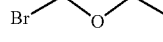 | H | 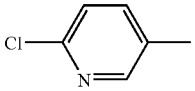 | NO$_2$ | H | 1 | 98 | 100 | 100 | 100 |
| 56 | 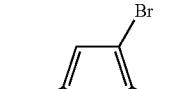 | H | 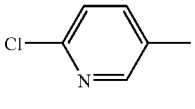 | NO$_2$ | H | 1 | 100 | 100 | 100 | 100 |
| 57 | 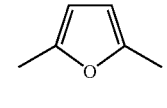 | H | 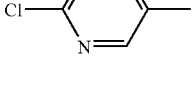 | NO$_2$ | H | 1 | 100 | 78 | 100 | 100 |
| 58 | 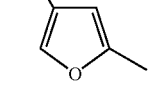 | H | 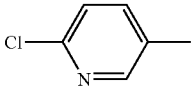 | NO$_2$ | H | 1 | 86 | 65 | 98 | 100 |
| 59 | 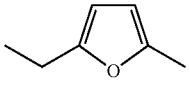 | H | 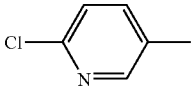 | NO$_2$ | H | 1 | 57 | 84 | 86 | 100 |
| 60 | 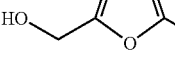 | H | 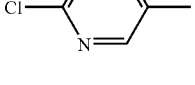 | NO$_2$ | H | 1 | 47 | 56 | 84 | 100 |
| 61 | 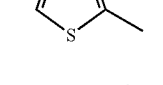 | H | 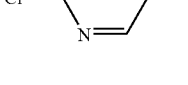 | NO$_2$ | H | 1 | 100 | 100 | 100 | 100 |
| 62 | 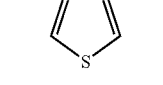 | H | 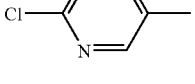 | NO$_2$ | H | 1 | 90 | 100 | 100 | 100 |
| 63 | 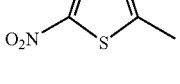 | H |  | NO$_2$ | H | 1 | 98 | 100 | 100 | 100 |

TABLE 1-continued

Insecticidal activities of compounds (I)

(I)

|  |  |  |  |  |  |  | Insecticidal activities | | | |
|---|---|---|---|---|---|---|---|---|---|---|
|  |  |  |  |  |  |  | *Aphis craccivoral* Mortality (%) 500 ppm | *Nilaparvata lugens* Mortality (%) 500 ppm | *Pseudaletia separate* Walker Mortality (%) 500 ppm | *Plutella xylostella* Mortality (%) 500 ppm |
| Compd. | R₁ | R₂ | Z | Y | R₅ | n | | | | |
| 64 | 2-Cl-pyridin-5-yl | H | 5-Cl-thien-2-yl | NO₂ | H | 1 | 100 | 100 | 100 | 100 |
| 65 | 2-Cl-pyridin-5-yl | H | 5-Br-thien-2-yl | NO₂ | H | 1 | 73 | 100 | 92 | 100 |
| 66 | 2-Cl-pyridin-5-yl | H | 4-Cl-thien-2-yl | NO₂ | H | 1 | 56 | 87 | 87 | 100 |
| 67 | 2-Cl-pyridin-5-yl | H | 4-Br-thien-2-yl | NO₂ | H | 1 | 65 | 83 | 90 | 100 |
| 68 | 2-Cl-thiazol-5-yl | H | fur-2-yl | NO₂ | H | 0 | 100 | 100 | 100 | 100 |
| 69 | 2-Cl-thiazol-5-yl | H | fur-3-yl | NO₂ | H | 0 | 100 | 100 | 100 | 100 |
| 70 | 2-Cl-thiazol-5-yl | H | 5-NO₂-fur-2-yl | NO₂ | H | 0 | 100 | 100 | 98 | 100 |
| 71 | 2-Cl-thiazol-5-yl | H | 5-Cl-fur-2-yl | NO₂ | H | 0 | 100 | 100 | 100 | 100 |
| 72 | 2-Cl-thiazol-5-yl | H | 5-Br-fur-2-yl | NO₂ | H | 0 | 100 | 100 | 100 | 100 |

TABLE 1-continued
Insecticidal activities of compounds (I)
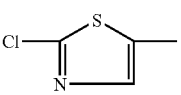
(I)
| Compd. | R$_1$ | R$_2$ | Z | Y | R$_5$ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 73 | 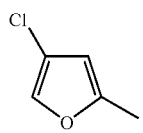 | H | 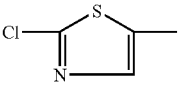 | NO$_2$ | H | 0 | 100 | 100 | 100 | 100 |
| 74 | 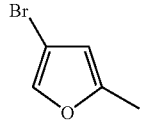 | H | 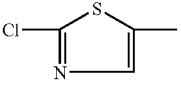 | NO$_2$ | H | 0 | 100 | 100 | 100 | 100 |
| 75 | 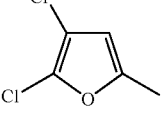 | H | 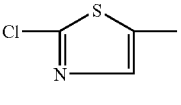 | NO$_2$ | H | 0 | 100 | 100 | 100 | 100 |
| 76 | 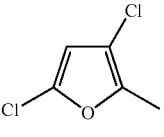 | H | 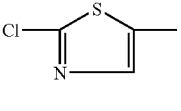 | NO$_2$ | H | 0 | 100 | 100 | 100 | 100 |
| 77 | 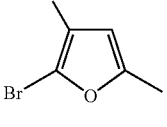 | H | 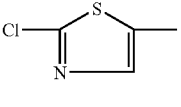 | NO$_2$ | H | 0 | 100 | 100 | 100 | 100 |
| 78 | 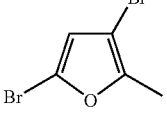 | H | 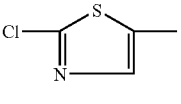 | NO$_2$ | H | 0 | 100 | 100 | 100 | 100 |
| 79 | 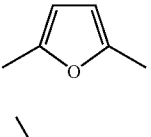 | H | 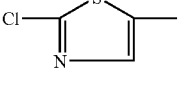 | NO$_2$ | H | 0 | 100 | 100 | 100 | 100 |
| 80 | 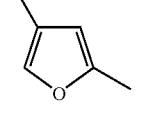 | H | | NO$_2$ | H | 0 | 100 | 100 | 100 | 100 |

TABLE 1-continued

Insecticidal activities of compounds (I)

(I)

| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 81 | 2-Cl-thiazol-5-yl | H | 5-ethyl-furan-2-yl | $NO_2$ | H | 0 | 100 | 100 | 100 | 100 |
| 82 | 2-Cl-thiazol-5-yl | H | 5-(hydroxymethyl)-furan-2-yl | $NO_2$ | H | 0 | 100 | 100 | 100 | 100 |
| 83 | 2-Cl-thiazol-5-yl | H | thiophen-2-yl | $NO_2$ | H | 0 | 100 | 100 | 100 | 100 |
| 84 | 2-Cl-thiazol-5-yl | H | 3-methyl-thiophen-2-yl | $NO_2$ | H | 0 | 100 | 100 | 100 | 100 |
| 85 | 2-Cl-thiazol-5-yl | H | 5-nitro-thiophen-2-yl | $NO_2$ | H | 0 | 100 | 100 | 100 | 100 |
| 86 | 2-Cl-thiazol-5-yl | H | 5-chloro-thiophen-2-yl | $NO_2$ | H | 0 | 100 | 100 | 100 | 100 |
| 87 | 2-Cl-thiazol-5-yl | H | 5-bromo-thiophen-2-yl | $NO_2$ | H | 0 | 100 | 100 | 100 | 100 |
| 88 | 2-Cl-thiazol-5-yl | H | 4-chloro-thiophen-2-yl | $NO_2$ | H | 0 | 100 | 100 | 100 | 100 |
| 89 | 2-Cl-thiazol-5-yl | H | 4-bromo-thiophen-2-yl | $NO_2$ | H | 0 | 100 | 100 | 97 | 100 |
| 91 | tetrahydrofuran-3-yl | H | furan-2-yl | $NO_2$ | H | 0 | 87 | 100 | 98 | 100 |

TABLE 1-continued
Insecticidal activities of compounds (I)
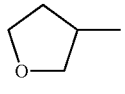
(I)
| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 92 | 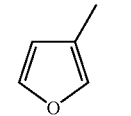 | H | 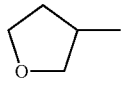 | NO₂ | H | 0 | 80 | 100 | 100 | 100 |
| 93 | 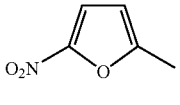 | H | 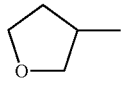 | NO₂ | H | 0 | 78 | 87 | 100 | 96 |
| 94 | 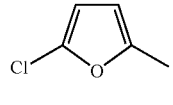 | H | 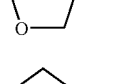 | NO₂ | H | 0 | 46 | 77 | 77 | 83 |
| 95 | 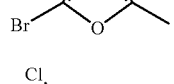 | H | 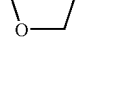 | NO₂ | H | 0 | 65 | 61 | 87 | 92 |
| 96 | 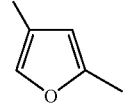 | H | 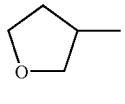 | NO₂ | H | 0 | 32 | 50 | 58 | 52 |
| 97 | 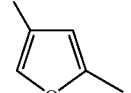 | H | 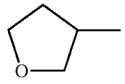 | NO₂ | H | 0 | 76 | 88 | 90 | 86 |
| 98 | 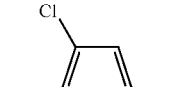 | H | 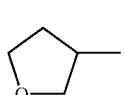 | NO₂ | H | 0 | 76 | 90 | 68 | 77 |
| 99 | 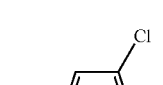 | H | 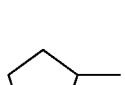 | NO₂ | H | 0 | 87 | 97 | 100 | 100 |
| 100 | 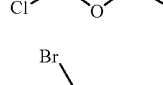 | H |  | NO₂ | H | 0 | 90 | 100 | 100 | 100 |

TABLE 1-continued

Insecticidal activities of compounds (I)

(I)

|  |  |  |  |  |  |  | Insecticidal activities | | | |
|---|---|---|---|---|---|---|---|---|---|---|
|  |  |  |  |  |  |  | *Aphis craccivoral* Mortality (%) 500 ppm | *Nilaparvata lugens* Mortality (%) 500 ppm | *Pseudaletia separate* Walker Mortality (%) 500 ppm | *Plutella xylostella* Mortality (%) 500 ppm |
| Compd. | R₁ | R₂ | Z | Y | R₅ | n |  |  |  |  |
| 101 | (3-methyltetrahydrofuran) | H | (5-ethylfuran-2-yl) | NO₂ | H | 0 | 76 | 65 | 65 | 78 |
| 102 | (3-methyltetrahydrofuran) | H | (5-(hydroxymethyl)furan-2-yl) | NO₂ | H | 0 | 75 | 89 | 89 | 97 |
| 103 | (phenyl) | H | (2-methylfuran) | NO₂ | H | 0 | 86 | 100 | 70 | 25 |
| 104 | (phenyl) | H | (3-methylfuran) | NO₂ | H | 0 | 96 | 100 | 79 | 81 |
| 105 | (phenyl) | H | (5-methyl-2-nitrofuran) | NO₂ | H | 0 | 80 | 100 | 98 | 90 |
| 106 | (phenyl) | H | (4-chloro-5-methylfuran) | NO₂ | H | 0 | 91 | 87 | 59 | 75 |
| 107 | (phenyl) | H | (4-bromo-5-methylfuran) | NO₂ | H | 0 | 82 | 92 | 96 | 85 |
| 108 | (phenyl) | H | (4,5-dichloro-2-methylfuran) | NO₂ | H | 0 | 87 | 95 | 24 | 24 |
| 109 | (phenyl) | H | (3,5-dichloro-2-methylfuran) | NO₂ | H | 0 | 91 | 100 | 60 | 56 |

TABLE 1-continued

Insecticidal activities of compounds (I)

(I) Structure: R2, Z, R5, R1, Y, N, N with (n) bridge

| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 110 | phenyl | H | 2,3-dibromo-5-methylfuran-yl | NO₂ | H | 0 | 58 | 23 | 85 | 51 |
| 111 | 6-chloropyridin-3-yl | CH₃ | 5-methylfuran-2-yl | NO₂ | H | 0 | 45 | 53 | 77 | 25 |
| 112 | 6-chloropyridin-3-yl | CH₃ | 4-methylfuran-3-yl | NO₂ | H | 0 | 56 | 76 | 68 | 53 |
| 113 | 6-chloropyridin-3-yl | CH₃ | 5-methyl-2-nitrofuran-yl | NO₂ | H | 0 | 80 | 100 | 100 | 100 |
| 114 | 6-chloropyridin-3-yl | CH₃ | 2,5-dimethylfuran-yl | NO₂ | H | 0 | 92 | 100 | 10 | 30 |
| 115 | 6-chloropyridin-3-yl | CH₃ | 2-ethyl-5-methylfuran-yl | NO₂ | H | 0 | 93 | 100 | 79 | 96 |
| 116 | 6-chloropyridin-3-yl | CH₃ | 4-methylthiophen-3-yl | NO₂ | H | 0 | 89 | 94 | 76 | 64 |
| 117 | 6-chloropyridin-3-yl | CH₃ | 5-methyl-2-nitrothiophen-yl | NO₂ | H | 0 | 83 | 88 | 77 | 86 |
| 118 | 6-chloropyridin-3-yl | CH₃ | 5-chloro-2-methylthiophen-yl | NO₂ | H | 0 | 93 | 90 | 19 | 23 |
| 119 | 6-chloropyridin-3-yl | CH₃ | 5-bromo-2-methylthiophen-yl | NO₂ | H | 0 | 75 | 91 | 46 | 87 |

TABLE 1-continued

Insecticidal activities of compounds (I)

(I)

| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 120 | 6-Cl-pyridin-3-yl | CH₃ | 4-Cl-5-methylthien-2-yl | NO₂ | H | 0 | 52 | 86 | 59 | 68 |
| 121 | 6-Cl-pyridin-3-yl | H | 5-methylfuran-2-yl | NO₂ | CH₃ | 0 | 100 | 100 | 100 | 56 |
| 123 | 6-Cl-pyridin-3-yl | H | 4-methylfuran-3-yl | NO₂ | CH₃ | 0 | 100 | 100 | 100 | 100 |
| 124 | 6-Cl-pyridin-3-yl | H | 5-methyl-2-nitrofuran-2-yl | NO₂ | CH₃ | 0 | 100 | 100 | 100 | 100 |
| 125 | 6-Cl-pyridin-3-yl | H | 5-Cl-2-methylfuran-2-yl | NO₂ | CH₃ | 0 | 100 | 100 | 98 | 100 |
| 126 | 6-Cl-pyridin-3-yl | H | 5-Br-2-methylfuran-2-yl | NO₂ | CH₃ | 0 | 100 | 100 | 100 | 100 |
| 127 | 6-Cl-pyridin-3-yl | H | 5-methylthien-2-yl | NO₂ | CH₃ | 0 | 100 | 100 | 100 | 100 |
| 128 | 6-Cl-pyridin-3-yl | H | 4-methylthien-3-yl | NO₂ | CH₃ | 0 | 100 | 100 | 100 | 100 |
| 129 | 6-Cl-pyridin-3-yl | H | 5-methyl-2-nitrothien-2-yl | NO₂ | CH₃ | 0 | 100 | 100 | 100 | 80 |
| 130 | 6-Cl-pyridin-3-yl | H | 5-Cl-2-methylthien-2-yl | NO₂ | CH₃ | 0 | 100 | 100 | 100 | 76 |

TABLE 1-continued

Insecticidal activities of compounds (I)

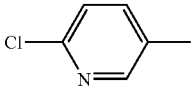

(I)

| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 131 | 6-Cl-pyridin-3-yl | H | 1H-pyrrol-2-yl | $NO_2$ | $CH_3$ | 0 | 100 | 100 | 100 | 63 |
| 132 | 6-Cl-pyridin-3-yl | H | 1H-pyrrol-2-yl | $NO_2$ | $C_2H_5$ | 0 | 73 | 84 | 89 | 99 |
| 133 | 6-Cl-pyridin-3-yl | $CH_3$ | furan-2-yl | $NO_2$ | $CH_3$ | 0 | 48 | 50 | 90 | 68 |
| 134 | 6-Cl-pyridin-3-yl | $CH_3$ | furan-3-yl | $NO_2$ | $CH_3$ | 0 | 38 | 51 | 52 | 46 |
| 135 | 6-Cl-pyridin-3-yl | $CH_3$ | 5-nitro-furan-2-yl | $NO_2$ | $CH_3$ | 0 | 56 | 63 | 45 | 56 |
| 136 | 6-Cl-pyridin-3-yl | $CH_3$ | 5-chloro-furan-2-yl | $NO_2$ | $CH_3$ | 0 | 100 | 100 | 100 | 100 |
| 137 | 6-Cl-pyridin-3-yl | $CH_3$ | 5-bromo-furan-2-yl | $NO_2$ | $CH_3$ | 0 | 98 | 100 | 100 | 100 |
| 138 | 6-Cl-pyridin-3-yl | $CH_3$ | thiophen-2-yl | $NO_2$ | $CH_3$ | 0 | 100 | 100 | 100 | 100 |
| 139 | 6-Cl-pyridin-3-yl | $CH_3$ | thiophen-3-yl | $NO_2$ | $CH_3$ | 0 | 93 | 100 | 95 | 100 |
| 140 | 6-Cl-pyridin-3-yl | H | furan-2-yl | CN | H | 0 | 100 | 100 | 100 | 100 |

TABLE 1-continued
Insecticidal activities of compounds (I)
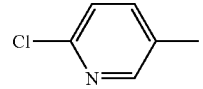
| Compd. | R₁ | R₂ | Z | Y | R₅ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|
| 141 | 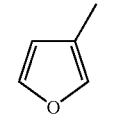 | H | 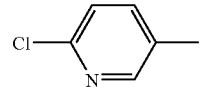 | CN | H | 0 | 100 | 100 | 100 | 100 |
| 142 | 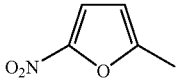 | H | 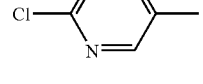 | CN | H | 0 | 100 | 100 | 100 | 100 |
| 143 | 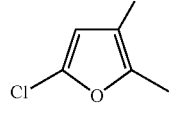 | H | 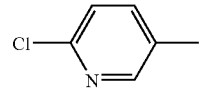 | CN | H | 0 | 75 | 100 | 86 | 85 |
| 144 | 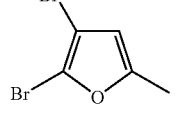 | H | 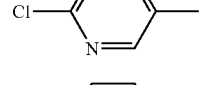 | CN | H | 0 | 87 | 100 | 90 | 100 |
| 145 | 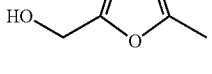 | H | 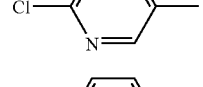 | CN | H | 0 | 92 | 100 | 100 | 100 |
| 146 | 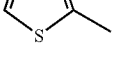 | H | 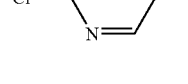 | CN | H | 0 | 100 | 100 | 100 | 100 |
| 147 | 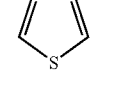 | H | 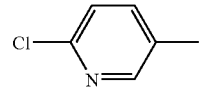 | CN | H | 0 | 100 | 100 | 100 | 100 |
| 148 | 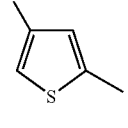 | H | 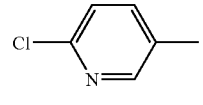 | CN | H | 0 | 97 | 100 | 100 | 100 |
| 149 | 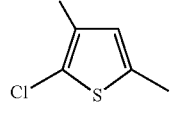 | H | | CN | H | 0 | 94 | 100 | 97 | 100 |

TABLE 1-continued

Insecticidal activities of compounds (I)

(I)

|  |  |  |  |  |  |  | Insecticidal activities | | | |
|---|---|---|---|---|---|---|---|---|---|---|
|  |  |  |  |  |  |  | *Aphis craccivoral* Mortality (%) | *Nilaparvata lugens* Mortality (%) | *Pseudaletia separate* Walker Mortality (%) | *Plutella xylostella* Mortality (%) |
| Compd. | R₁ | R₂ | Z | Y | R₅ | n | 500 ppm | 500 ppm | 500 ppm | 500 ppm |
| 150 | 2-chloro-5-pyridyl | H | 3,5-dichloro-2-thienyl | CN | H | 0 | 95 | 100 | 100 | 100 |

TABLE 2

Insecticidal activities of compounds (II)

(II)

|  |  |  |  |  |  |  |  |  | Insecticidal activities | | | |
|---|---|---|---|---|---|---|---|---|---|---|---|---|
|  |  |  |  |  |  |  |  |  | *Aphis craccivoral* Mortality (%) | *Nilaparvata lugens* Mortality (%) | *Pseudaletia separate* Walker Mortality (%) | *Plutella xylostella* Mortality (%) |
| Compd. | R₁ | R₂ | R₃ | R₄ | Z | Y | R₅ | | 500 ppm | 500 ppm | 500 ppm | 500 ppm |
| 151 | 2-chloro-5-pyridyl | H | H | CH₃ | 2-furyl | NO₂ | H | | 76 | 87 | 86 | 79 |
| 152 | 2-chloro-5-pyridyl | H | H | CH₃ | 3-furyl | NO₂ | H | | 67 | 64 | 80 | 40 |
| 153 | 2-chloro-5-pyridyl | H | H | CH₃ | 5-nitro-2-furyl | NO₂ | H | | 56 | 87 | 90 | 100 |
| 154 | 2-chloro-5-pyridyl | H | H | CH₃ | 5-chloro-2-furyl | NO₂ | H | | 52 | 65 | 100 | 100 |

TABLE 2-continued

Insecticidal activities of compounds (II)

(II)

|  |  |  |  |  |  |  |  | Insecticidal activities | | | |
|---|---|---|---|---|---|---|---|---|---|---|---|
| Compd. | R₁ | R₂ | R₃ | R₄ | Z | Y | R₅ | *Aphis cracci voral* Mortality (%) 500 ppm | *Nilapar vata lugens* Mortality (%) 500 ppm | *Pseuda letia separate* Walker Mortality (%) 500 ppm | *Plutella xylostella* Mortality (%) 500 ppm |
| 155 | 6-Cl-pyridin-3-yl | H | H | CH₃ | 5-Br-furan-2-yl | NO₂ | H | 67 | 36 | 97 | 100 |
| 156 | 6-Cl-pyridin-3-yl | H | H | CH₃ | thiophen-2-yl | NO₂ | H | 89 | 90 | 100 | 100 |
| 157 | 6-Cl-pyridin-3-yl | H | H | CH₃ | thiophen-3-yl | NO₂ | H | 100 | 97 | 100 | 100 |
| 158 | 6-Cl-pyridin-3-yl | H | H | CH₃ | 5-NO₂-thiophen-2-yl | NO₂ | H | 43 | 43 | 67 | 24 |
| 159 | 6-Cl-pyridin-3-yl | H | H | CH₃ | 5-Cl-thiophen-2-yl | NO₂ | H | 55 | 67 | 78 | 75 |
| 160 | 6-Cl-pyridin-3-yl | H | H | CH₃ | 1H-pyrrol-2-yl | NO₂ | H | 56 | 54 | 64 | 100 |
| 161 | 6-Cl-pyridin-3-yl | H | CH₃ | CH₃ | furan-2-yl | NO₂ | H | 100 | 65 | 100 | 100 |
| 162 | 6-Cl-pyridin-3-yl | H | CH₃ | CH₃ | furan-3-yl | NO₂ | H | 100 | 100 | 100 | 100 |
| 163 | 6-Cl-pyridin-3-yl | H | CH₃ | CH₃ | 5-NO₂-furan-2-yl | NO₂ | H | 100 | 100 | 100 | 100 |
| 164 | 6-Cl-pyridin-3-yl | H | CH₃ | CH₃ | 5-Cl-furan-2-yl | NO₂ | H | 100 | 100 | 100 | 100 |

TABLE 2-continued

Insecticidal activities of compounds (II)

(II)

| Compd. | R₁ | R₂ | R₃ | R₄ | Z | Y | R₅ | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|
| 165 | 6-Cl-pyridin-3-yl | H | CH₃ | CH₃ | 5-bromo-furan-2-yl | NO₂ | H | 100 | 100 | 100 | 100 |
| 166 | 6-Cl-pyridin-3-yl | H | CH₃ | CH₃ | thien-2-yl | NO₂ | H | 98 | 100 | 100 | 100 |
| 167 | 6-Cl-pyridin-3-yl | H | CH₃ | CH₃ | thien-3-yl | NO₂ | H | 100 | 100 | 100 | 100 |
| 168 | 6-Cl-pyridin-3-yl | H | CH₃ | CH₃ | 5-nitro-thien-2-yl | NO₂ | H | 80 | 90 | 100 | 100 |
| 169 | 6-Cl-pyridin-3-yl | H | CH₃ | CH₃ | 5-chloro-thien-2-yl | NO₂ | H | 76 | 67 | 97 | 100 |
| 170 | 6-Cl-pyridin-3-yl | H | CH₃ | CH₃ | pyrrol-2-yl | NO₂ | H | 89 | 34 | 100 | 100 |
| 171 | 6-Cl-pyridin-3-yl | H | CH₃ | C₂H₅ | furan-3-yl | NO₂ | H | 93 | 100 | 100 | 100 |
| 172 | 6-Cl-pyridin-3-yl | H | CH₃ | C₂H₅ | 5-nitro-furan-2-yl | NO₂ | H | 96 | 100 | 100 | 100 |
| 173 | 6-Cl-pyridin-3-yl | H | CH₃ | C₂H₅ | 5-chloro-furan-2-yl | NO₂ | H | 87 | 85 | 100 | 100 |
| 174 | 6-Cl-pyridin-3-yl | H | CH₃ | C₂H₅ | 5-bromo-furan-2-yl | NO₂ | H | 100 | 100 | 100 | 100 |

TABLE 2-continued

Insecticidal activities of compounds (II)

(II)

| Compd. | R₁ | R₂ | R₃ | R₄ | Z | Y | R₅ | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|
| 175 | 6-chloropyridin-3-yl | H | CH₃ | C₂H₅ | thiophen-2-yl | NO₂ | H | 100 | 100 | 100 | 100 |
| 176 | 6-chloropyridin-3-yl | H | CH₃ | C₂H₅ | 5-nitrothiophen-2-yl | NO₂ | H | 86 | 100 | 45 | 84 |
| 177 | 6-chloropyridin-3-yl | H | CH₃ | C₂H₅ | 5-chlorothiophen-2-yl | NO₂ | H | 87 | 100 | 64 | 53 |
| 178 | 6-chloropyridin-3-yl | H | CH₃ | C₂H₅ | 1H-pyrrol-2-yl | NO₂ | H | 100 | 100 | 100 | 100 |
| 179 | 6-chloropyridin-3-yl | H | C₂H₅ | CH₃ | furan-2-yl | NO₂ | H | 100 | 100 | 98 | 100 |
| 180 | 6-chloropyridin-3-yl | H | C₂H₅ | CH₃ | furan-3-yl | NO₂ | H | 100 | 100 | 100 | 100 |
| 181 | 6-chloropyridin-3-yl | H | C₂H₅ | CH₃ | 5-nitrofuran-2-yl | NO₂ | H | 100 | 100 | 100 | 100 |
| 182 | 6-chloropyridin-3-yl | H | C₂H₅ | CH₃ | 5-chlorofuran-2-yl | NO₂ | H | 100 | 100 | 100 | 100 |
| 183 | 6-chloropyridin-3-yl | H | C₂H₅ | CH₃ | 5-bromofuran-2-yl | NO₂ | H | 100 | 100 | 100 | 100 |
| 184 | 6-chloropyridin-3-yl | H | C₂H₅ | CH₃ | thiophen-2-yl | NO₂ | H | 98 | 100 | 100 | 100 |

TABLE 2-continued

Insecticidal activities of compounds (II)

(II)

[Structure: compound (II) with substituents R1, R2, R3, R4, R5, Y, Z, N=N]

| Compd. | R1 | R2 | R3 | R4 | Z | Y | R5 | Aphis cracci-voral Mortality (%) 500 ppm | Nilapar-vata lugens Mortality (%) 500 ppm | Pseuda-letia separate Walker Mortality (%) 500 ppm | Plutella xylostella Mortality (%) 500 ppm |
|---|---|---|---|---|---|---|---|---|---|---|---|
| 185 | 2-Cl-5-pyridyl | H | C2H5 | CH3 | 3-thienyl | NO2 | H | 100 | 100 | 100 | 100 |
| 186 | 2-Cl-5-pyridyl | H | C2H5 | CH3 | 5-nitro-2-thienyl | NO2 | H | 100 | 100 | 100 | 100 |
| 187 | 2-Cl-5-pyridyl | H | C2H5 | CH3 | 5-chloro-2-thienyl | NO2 | H | 100 | 100 | 100 | 100 |
| 188 | 2-Cl-5-pyridyl | H | C2H5 | CH3 | 2-pyrrolyl | NO2 | H | 100 | 100 | 100 | 100 |
| 189 | 2-Cl-5-pyridyl | H | C2H5 | C2H5 | 2-furyl | NO2 | H | 86 | 100 | 89 | 93 |
| 190 | 2-Cl-5-pyridyl | H | C2H5 | C2H5 | 3-furyl | NO2 | H | 87 | 100 | 45 | 59 |
| 191 | 2-Cl-5-pyridyl | H | C2H5 | C2H5 | 5-nitro-2-furyl | NO2 | H | 95 | 100 | 76 | 62 |
| 192 | 2-Cl-5-pyridyl | H | C2H5 | C2H5 | 5-chloro-2-furyl | NO2 | H | 97 | 100 | 67 | 57 |
| 193 | 2-Cl-5-pyridyl | H | C2H5 | C2H5 | 5-bromo-2-furyl | NO2 | H | 89 | 100 | 56 | 11 |
| 194 | 2-Cl-5-pyridyl | CH3 | CH3 | CH3 | 2-pyrrolyl | NO2 | H | 98 | 100 | 100 | 100 |

TABLE 2-continued

Insecticidal activities of compounds (II)

(II)

| Compd. | R₁ | R₂ | R₃ | R₄ | Z | Y | R₅ | Aphis cracci-voral Mortality (%) 500 ppm | Nilapar-vata lugens Mortality (%) 500 ppm | Pseuda-letia separate Walker Mortality (%) 500 ppm | Plutella xylostella Mortality (%) 500 ppm |
|---|---|---|---|---|---|---|---|---|---|---|---|
| 195 | 6-Cl-pyridin-3-yl | CH₃ | C₂H₅ | CH₃ | 5-methylfuran-2-yl | NO₂ | H | 100 | n.t. | 100 | 100 |
| 196 | 6-Cl-pyridin-3-yl | CH₃ | C₂H₅ | CH₃ | 4-methylfuran-3-yl | NO₂ | H | 100 | 100 | 100 | 98 |
| 197 | 6-Cl-pyridin-3-yl | CH₃ | C₂H₅ | CH₃ | 5-methyl-2-nitrofuran-2-yl | NO₂ | H | 98 | 100 | 86 | 53 |
| 198 | 6-Cl-pyridin-3-yl | CH₃ | C₂H₅ | CH₃ | 5-chloro-2-methylfuran-3-yl | NO₂ | H | 86 | 100 | 57 | 65 |
| 199 | 6-Cl-pyridin-3-yl | CH₃ | C₂H₅ | CH₃ | 5-bromo-2-methylfuran-3-yl | NO₂ | H | 84 | 100 | 47 | 98 |
| 200 | 6-Cl-pyridin-3-yl | CH₃ | C₂H₅ | CH₃ | 5-methylthiophen-2-yl | NO₂ | H | 100 | 100 | 100 | 100 |
| 201 | 6-Cl-pyridin-3-yl | CH₃ | C₂H₅ | CH₃ | 4-methylthiophen-3-yl | NO₂ | H | 100 | 100 | 90 | 100 |
| 202 | 6-Cl-pyridin-3-yl | CH₃ | C₂H₅ | CH₃ | 5-methyl-2-nitrothiophen-2-yl | NO₂ | H | 100 | 100 | 98 | 100 |
| 203 | 6-Cl-pyridin-3-yl | CH₃ | C₂H₅ | CH₃ | 5-chloro-2-methylthiophen-3-yl | NO₂ | H | 100 | 100 | 100 | 100 |
| 204 | 6-Cl-pyridin-3-yl | CH₃ | C₂H₅ | CH₃ | 5-methyl-1H-pyrrol-2-yl | NO₂ | H | 92 | 100 | 73 | 78 |

TABLE 2-continued

Insecticidal activities of compounds (II)

(II)

Structure: R1-CH(R5)-N(R3)-C(=N-R4)-C(Y)=C(R2)-Z

| Compd. | R₁ | R₂ | R₃ | R₄ | Z | Y | R₅ | *Aphis craccivoral* Mortality (%) 500 ppm | *Nilaparvata lugens* Mortality (%) 500 ppm | *Pseudaletia separate* Walker Mortality (%) 500 ppm | *Plutella xylostella* Mortality (%) 500 ppm |
|---|---|---|---|---|---|---|---|---|---|---|---|
| 205 | 6-Cl-pyridin-3-yl | H | C₂H₅ | CH₃ | furan-2-yl | NO₂ | CH₃ | 56 | 87 | 87 | 65 |
| 206 | 6-Cl-pyridin-3-yl | H | C₂H₅ | CH₃ | furan-3-yl | NO₂ | CH₃ | 65 | 44 | 90 | 100 |
| 207 | 6-Cl-pyridin-3-yl | H | C₂H₅ | CH₃ | 5-O₂N-furan-2-yl | NO₂ | CH₃ | 94 | 100 | 100 | 100 |
| 208 | 6-Cl-pyridin-3-yl | H | C₂H₅ | CH₃ | 5-Cl-furan-2-yl | NO₂ | CH₃ | 42 | 100 | 73 | 45 |
| 209 | 6-Cl-pyridin-3-yl | H | C₂H₅ | CH₃ | 5-Br-furan-2-yl | NO₂ | CH₃ | 88 | 100 | 98 | 100 |
| 210 | 6-Cl-pyridin-3-yl | H | C₂H₅ | CH₃ | thiophen-2-yl | NO₂ | CH₃ | 100 | 100 | 100 | 100 |
| 211 | 6-Cl-pyridin-3-yl | H | C₂H₅ | CH₃ | 1H-pyrrol-2-yl | NO₂ | CH₃ | 73 | 73 | 94 | 100 |
| 212 | 6-Cl-pyridin-3-yl | CH₃ | CH₃ | CH₃ | 5-O₂N-furan-2-yl | NO₂ | CH₃ | 96 | 100 | 78 | 59 |
| 213 | 6-Cl-pyridin-3-yl | CH₃ | CH₃ | CH₃ | thiophen-3-yl | NO₂ | CH₃ | 89 | 68 | 76 | 54 |
| 214 | 6-Cl-pyridin-3-yl | CH₃ | CH₃ | CH₃ | 5-O₂N-thiophen-2-yl | NO₂ | CH₃ | 98 | 100 | 93 | 100 |

TABLE 2-continued

Insecticidal activities of compounds (II)

$$\text{Structure (II): } R_1\text{-CH}(R_5)\text{-N}(R_3)\text{-C}(=\text{N}R_4)\text{-C}(Y)=\text{C}(R_2)\text{-Z}$$

| Compd. | R₁ | R₂ | R₃ | R₄ | Z | Y | R₅ | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|
| 215 | 6-chloro-pyridin-3-yl | CH₃ | CH₃ | CH₃ | 5-chloro-thiophen-2-yl | NO₂ | CH₃ | 100 | 100 | 100 | 100 |
| 216 | 6-chloro-pyridin-3-yl | CH₃ | CH₃ | CH3 | 1H-pyrrol-2-yl | NO₂ | CH₃ | 100 | 100 | 100 | 100 |
| 217 | 2-chloro-thiazol-5-yl | H | CH₃ | CH₃ | 5-nitro-furan-2-yl | NO₂ | H | 77 | 43 | 88 | 63 |
| 218 | 2-chloro-thiazol-5-yl | H | CH₃ | CH₃ | 5-chloro-furan-2-yl | NO₂ | H | 88 | 86 | 97 | 100 |
| 219 | 2-chloro-thiazol-5-yl | H | CH₃ | CH₃ | 5-bromo-furan-2-yl | NO₂ | H | 87 | 87 | 98 | 100 |
| 220 | 2-chloro-thiazol-5-yl | H | CH₃ | CH₃ | thiophen-2-yl | NO₂ | H | 80 | 67 | 100 | 100 |
| 221 | 2-chloro-thiazol-5-yl | H | CH₃ | CH₃ | thiophen-3-yl | NO₂ | H | 78 | 87 | 100 | 95 |
| 222 | 2-chloro-thiazol-5-yl | H | CH₃ | CH₃ | 5-nitro-thiophen-2-yl | NO₂ | H | 46 | 67 | 77 | 98 |
| 223 | 2-chloro-thiazol-5-yl | H | CH₃ | CH₃ | 5-chloro-thiophen-2-yl | NO₂ | H | 65 | 53 | 87 | 86 |
| 224 | 2-chloro-thiazol-5-yl | H | CH₃ | CH₃ | 1H-pyrrol-2-yl | NO₂ | H | 32 | 52 | 58 | 65 |

TABLE 2-continued

Insecticidal activities of compounds (II)

(II)

| Compd. | R$_1$ | R$_2$ | R$_3$ | R$_4$ | Z | Y | R$_5$ | Aphis cracci-voral Mortality (%) 500 ppm | Nilapar-vata lugens Mortality (%) 500 ppm | Pseuda-letia separate Walker Mortality (%) 500 ppm | Plutella xylostella Mortality (%) 500 ppm |
|---|---|---|---|---|---|---|---|---|---|---|---|
| 225 | 2-Cl-thiazol-5-yl | H | C$_2$H$_5$ | CH$_3$ | furan-2-yl | NO$_2$ | H | 90 | 78 | 76 | 98 |
| 226 | 2-Cl-thiazol-5-yl | H | C$_2$H$_5$ | CH$_3$ | furan-3-yl | NO$_2$ | H | 68 | 49 | 76 | 80 |
| 227 | 2-Cl-thiazol-5-yl | H | C$_2$H$_5$ | CH$_3$ | 5-O$_2$N-furan-2-yl | NO$_2$ | H | 100 | 100 | 87 | 100 |
| 228 | 2-Cl-thiazol-5-yl | H | C$_2$H$_5$ | CH$_3$ | 5-Cl-furan-2-yl | NO$_2$ | H | 100 | 100 | 90 | 100 |
| 229 | 2-Cl-thiazol-5-yl | H | C$_2$H$_5$ | CH$_3$ | 5-O$_2$N-thien-2-yl | NO$_2$ | H | 65 | 75 | 76 | 35 |
| 230 | 2-Cl-thiazol-5-yl | H | C$_2$H$_5$ | CH$_3$ | 5-Cl-thien-2-yl | NO$_2$ | H | 75 | 50 | 89 | 33 |
| 231 | 2-Cl-thiazol-5-yl | H | C$_2$H$_5$ | CH$_3$ | pyrrol-2-yl | NO$_2$ | H | 37 | 76 | 53 | 87 |
| 232 | 6-Cl-pyridin-3-yl | H | CH$_3$ | CH$_3$ | furan-2-yl | NO$_2$ | H | 96 | 56 | 100 | 100 |
| 233 | 6-Cl-pyridin-3-yl | H | CH$_3$ | CH$_3$ | furan-3-yl | NO$_2$ | H | 80 | 86 | 98 | 100 |
| 234 | 6-Cl-pyridin-3-yl | H | CH$_3$ | CH$_3$ | 5-Cl-furan-2-yl | NO$_2$ | H | 37 | 44 | 50 | 41 |

TABLE 2-continued

Insecticidal activities of compounds (II)

(II)

|  |  |  |  |  |  |  |  | Insecticidal activities | | | |
|---|---|---|---|---|---|---|---|---|---|---|---|
| Compd. | R₁ | R₂ | R₃ | R₄ | Z | Y | R₅ | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
| 235 | 6-chloropyridin-3-yl | H | CH₃ | CH₃ | 5-bromofuran-2-yl | NO₂ | H | 91 | 86 | 99 | 100 |
| 236 | 6-chloropyridin-3-yl | H | CH₃ | CH₃ | thiophen-2-yl | NO₂ | H | 82 | 79 | 96 | 100 |
| 237 | 6-chloropyridin-3-yl | H | CH₃ | CH₃ | thiophen-3-yl | NO₂ | H | 87 | 98 | 100 | 100 |
| 238 | 6-chloropyridin-3-yl | H | CH₃ | CH₃ | 5-nitrothiophen-2-yl | NO₂ | H | 91 | 98 | 100 | 100 |
| 239 | 6-chloropyridin-3-yl | H | CH₃ | CH₃ | 5-chlorothiophen-2-yl | NO₂ | H | 58 | 34 | 85 | 56 |
| 240 | 6-chloropyridin-3-yl | H | CH₃ | CH₃ | 1H-pyrrol-2-yl | NO₂ | H | 77 | 68 | 45 | 86 |
| 241 | 6-chloropyridin-3-yl | H | C₂H₅ | CH₃ | furan-2-yl | NO₂ | H | 68 | 76 | 56 | 62 |
| 242 | 6-chloropyridin-3-yl | H | C₂H₅ | CH₃ | furan-3-yl | NO₂ | H | 100 | 100 | 80 | 87 |
| 243 | 6-chloropyridin-3-yl | H | C₂H₅ | CH₃ | 1H-pyrrol-2-yl | NO₂ | H | 96 | 100 | 100 | 100 |

TABLE 3

Insecticidal activities of compounds (III)

(III)

$$\text{structure with } R_2, Z, Y, R_5, R_1, N, N^+, R_6, X^-, n$$

| Compd. | R₁ | R₂ | Z | Y | R₅ | R₆ | X⁻ | n | *Aphis craccivoral* Mortality (%) 500 ppm | *Nilaparvata lugens* Mortality (%) 500 ppm | *Pseudaletia separate* Walker Mortality (%) 500 ppm | *Plutella xylostella* Mortality (%) 500 ppm |
|---|---|---|---|---|---|---|---|---|---|---|---|---|
| 244 | 6-Cl-pyridin-3-yl | H | 2-methylfuran-5-yl | NO₂ | H | CH₃ | Cl⁻ | 0 | 100 | 100 | 100 | 100 |
| 245 | 6-Cl-pyridin-3-yl | H | 3-methylfuran | NO₂ | H | CH₃ | Cl⁻ | 0 | 100 | 100 | 100 | 100 |
| 246 | 6-Cl-pyridin-3-yl | H | 2-NO₂-5-methylfuran | NO₂ | H | CH₃ | Cl⁻ | 0 | 100 | 100 | 100 | 100 |
| 247 | 6-Cl-pyridin-3-yl | H | 2-Cl-5-methylfuran | NO₂ | H | CH₃ | Cl⁻ | 0 | 100 | 100 | 100 | 100 |
| 248 | 6-Cl-pyridin-3-yl | H | 2-Br-5-methylfuran | NO₂ | H | CH₃ | Cl⁻ | 0 | 100 | 100 | 100 | 100 |
| 249 | 6-Cl-pyridin-3-yl | H | 3-Cl-5-methylfuran | NO₂ | H | CH₃ | Cl⁻ | 0 | 100 | 100 | 100 | 100 |
| 250 | 6-Cl-pyridin-3-yl | H | 3-Br-5-methylfuran | NO₂ | H | CH₃ | Cl⁻ | 0 | 100 | 100 | 100 | 100 |
| 251 | 6-Cl-pyridin-3-yl | H | 2,3-diCl-5-methylfuran | NO₂ | H | CH₃ | Cl⁻ | 0 | 100 | 100 | 100 | 100 |
| 252 | 6-Cl-pyridin-3-yl | H | 3,5-diCl-2-methylfuran | NO₂ | H | CH₃ | Cl⁻ | 0 | 100 | 100 | 100 | 100 |

TABLE 3-continued

Insecticidal activities of compounds (III)

(III)

| Compd. | R₁ | R₂ | Z | Y | R₅ | R₆ | X⁻ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|---|
| 253 | 6-chloropyridin-3-yl | H | 2,3-dibromo-5-furyl | NO₂ | H | CH₃ | Cl⁻ | 0 | 100 | 100 | 100 | 100 |
| 254 | 6-chloropyridin-3-yl | H | 3-bromo-5-furyl | NO₂ | H | CH₃ | Cl⁻ | 0 | 100 | 100 | 100 | 100 |
| 255 | 6-chloropyridin-3-yl | H | 2,5-dimethyl-3-furyl | NO₂ | H | CH₃ | Cl⁻ | 0 | 100 | 100 | 100 | 100 |
| 256 | 6-chloropyridin-3-yl | H | 2,4-dimethyl-5-furyl | NO₂ | H | CH₃ | Cl⁻ | 0 | 100 | 100 | 100 | 100 |
| 257 | 6-chloropyridin-3-yl | H | 2-ethyl-5-furyl | NO₂ | H | CH₃ | Cl⁻ | 0 | 100 | 100 | 100 | 100 |
| 258 | 6-chloropyridin-3-yl | H | 5-(hydroxymethyl)-2-furyl | NO₂ | H | CH₃ | Cl⁻ | 0 | 100 | 100 | 100 | 100 |
| 259 | 6-chloropyridin-3-yl | H | 2-thienyl | NO₂ | H | CH₃ | Cl⁻ | 0 | 100 | 100 | 100 | 100 |
| 260 | 6-chloropyridin-3-yl | H | 3-methyl-2-thienyl | NO₂ | H | CH₃ | Cl⁻ | 0 | 90 | 92 | 80 | 89 |
| 261 | 6-chloropyridin-3-yl | H | 5-nitro-2-thienyl | NO₂ | H | CH₃ | Cl⁻ | 0 | 100 | 100 | 100 | 100 |
| 262 | 6-chloropyridin-3-yl | H | 5-chloro-2-thienyl | NO₂ | H | CH₃ | Cl⁻ | 0 | 100 | 100 | 100 | 100 |

TABLE 3-continued

Insecticidal activities of compounds (III)

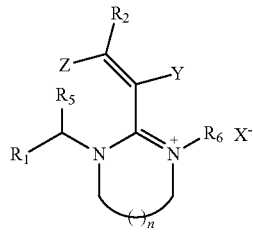

(III)

| Compd. | R₁ | R₂ | Z | Y | R₅ | R₆ | X⁻ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|---|
| 263 | 2-Cl-pyridin-5-yl | H | 5-Br-thiophen-2-yl | NO₂ | H | CH₃ | Cl⁻ | 0 | 100 | 100 | 100 | 100 |
| 264 | 2-Cl-pyridin-5-yl | H | 4-Cl-thiophen-2-yl | NO₂ | H | CH₃ | Cl⁻ | 0 | 100 | 100 | 100 | 100 |
| 265 | 2-Cl-pyridin-5-yl | H | 4-Br-thiophen-2-yl | NO₂ | H | CH₃ | Cl⁻ | 0 | 100 | 100 | 100 | 100 |
| 266 | 2-Cl-pyridin-5-yl | H | 4,5-diCl-thiophen-2-yl | NO₂ | H | CH₃ | Cl⁻ | 0 | 100 | 100 | 100 | 100 |
| 267 | 2-Cl-pyridin-5-yl | H | 3,5-diCl-thiophen-2-yl | NO₂ | H | CH₃ | Cl⁻ | 0 | 100 | 100 | 100 | 100 |
| 268 | 2-Cl-pyridin-5-yl | H | 4,5-diBr-thiophen-2-yl | NO₂ | H | CH₃ | Cl⁻ | 0 | 100 | 100 | 100 | 100 |
| 269 | 2-Cl-pyridin-5-yl | H | 3,5-diBr-thiophen-2-yl | NO₂ | H | CH₃ | Cl⁻ | 0 | 100 | 100 | 100 | 100 |
| 270 | 2-Cl-pyridin-5-yl | H | 5-Me-thiophen-2-yl | NO₂ | H | CH₃ | Cl⁻ | 0 | 100 | 100 | 100 | 100 |

TABLE 3-continued

Insecticidal activities of compounds (III)

(III)

[Structure showing compound (III) with R₁, R₂, R₅, R₆, Y, Z, X⁻, and n substituents on a cyclic amidinium framework]

| Compd. | R₁ | R₂ | Z | Y | R₅ | R₆ | X⁻ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|---|
| 271 | 6-Cl-pyridin-3-yl | H | 2,5-dimethylthien-3-yl | NO₂ | H | CH₃ | Cl⁻ | 0 | 100 | 100 | 100 | 100 |
| 272 | 6-Cl-pyridin-3-yl | H | 5-ethylthien-2-yl | NO₂ | H | CH₃ | Cl⁻ | 0 | 100 | 100 | 100 | 100 |
| 273 | 6-Cl-pyridin-3-yl | H | 5-(hydroxymethyl)thien-2-yl | NO₂ | H | CH₃ | Cl⁻ | 0 | 100 | 100 | 100 | 100 |
| 274 | 6-Cl-pyridin-3-yl | H | 1H-pyrrol-2-yl | NO₂ | H | CH₃ | Cl⁻ | 0 | 100 | 100 | 100 | 100 |
| 275 | 6-Cl-pyridin-3-yl | H | 1-methyl-1H-pyrrol-2-yl | NO₂ | H | CH₃ | Cl⁻ | 0 | 100 | 100 | 100 | 100 |
| 276 | 2-Cl-thiazol-5-yl | H | furan-3-yl | NO₂ | H | CH₃ | Cl⁻ | 0 | 100 | 100 | 100 | 100 |
| 277 | 2-Cl-thiazol-5-yl | H | 5-nitrofuran-2-yl | NO₂ | H | CH₃ | Cl⁻ | 0 | 100 | 100 | 100 | 100 |
| 278 | 2-Cl-thiazol-5-yl | H | 5-chlorofuran-2-yl | NO₂ | H | CH₃ | Cl⁻ | 0 | 100 | 100 | 100 | 100 |
| 279 | 2-Cl-thiazol-5-yl | H | 5-bromofuran-2-yl | NO₂ | H | CH₃ | Cl⁻ | 0 | 100 | 100 | 100 | 100 |
| 280 | 2-Cl-thiazol-5-yl | H | thien-2-yl | NO₂ | H | CH₃ | Cl⁻ | 0 | 100 | 100 | 100 | 100 |

TABLE 3-continued

Insecticidal activities of compounds (III)

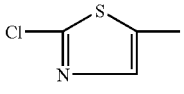

(III)

| Compd. | R₁ | R₂ | Z | Y | R₅ | R₆ | X⁻ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|---|
| 281 | 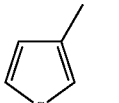 | H | 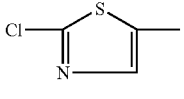 | NO₂ | H | CH₃ | Cl⁻ | 0 | 100 | 100 | 100 | 100 |
| 282 | 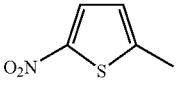 | H | 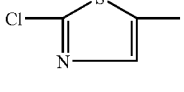 | NO₂ | H | CH₃ | Cl⁻ | 0 | 100 | 100 | 100 | 100 |
| 283 | 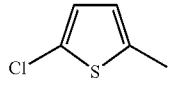 | H | 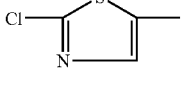 | NO₂ | H | CH₃ | Cl⁻ | 0 | 100 | 100 | 100 | 100 |
| 284 | 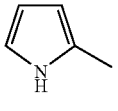 | H | 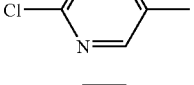 | NO₂ | H | CH₃ | Cl⁻ | 0 | 100 | 100 | 100 | 100 |
| 285 | 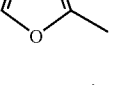 | H | 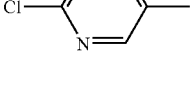 | NO₂ | H | C₂H₅ | Cl⁻ | 0 | 100 | 100 | 100 | 100 |
| 286 | 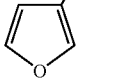 | H | 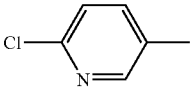 | NO₂ | H | C₂H₅ | Cl⁻ | 0 | 100 | 100 | 100 | 100 |
| 287 | 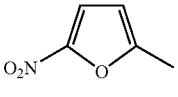 | H | 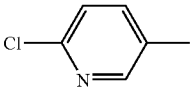 | NO₂ | H | C₂H₅ | Cl⁻ | 0 | 100 | 100 | 100 | 100 |
| 288 | 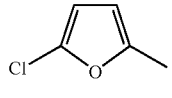 | H | 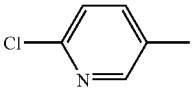 | NO₂ | H | C₂H₅ | Cl⁻ | 0 | 100 | 100 | 100 | 100 |
| 289 | 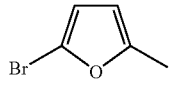 | H | 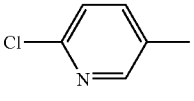 | NO₂ | H | C₂H₅ | Cl⁻ | 0 | 100 | 100 | 100 | 100 |
| 291 | 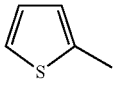 | H | | NO₂ | H | C₂H₅ | Cl⁻ | 0 | 100 | 100 | 100 | 100 |

TABLE 3-continued

Insecticidal activities of compounds (III)

| Compd. | R₁ | R₂ | Z | Y | R₅ | R₆ | X⁻ | n | Aphis craccivoral Mortality (%) 500 ppm | Nilaparvata lugens Mortality (%) 500 ppm | Pseudaletia separate Walker Mortality (%) 500 ppm | Plutella xylostella Mortality (%) 500 ppm |
|---|---|---|---|---|---|---|---|---|---|---|---|---|
| 292 | Cl-pyridyl | H | 3-methylthienyl | NO₂ | H | C₂H₅ | Cl⁻ | 0 | 100 | 100 | 100 | 100 |
| 293 | Cl-pyridyl | H | 5-methyl-2-nitrothienyl | NO₂ | H | C₂H₅ | Cl⁻ | 0 | 100 | 100 | 100 | 100 |
| 294 | Cl-pyridyl | H | 5-chloro-2-methylthienyl | NO₂ | H | C₂H₅ | Cl⁻ | 0 | 100 | 100 | 100 | 100 |
| 295 | Cl-pyridyl | H | 2-methylpyrrolyl | NO₂ | H | C₂H₅ | Cl⁻ | 0 | 100 | 100 | 100 | 100 |

Example 12

Preparation of Insecticidal Composition Comprising the Active Compounds of the Present Invention (a) Oily Suspension The following components were prepared: 25 wt % of compound selected from compounds 1-10; 5 wt % polyoxyethylene sorbital hexaoleate; and 70 wt % higher aliphatic hydrocarbon oil. All of the components were ground in a sand mill until the particle size of the solid particles was reduced to less than about 5 micrometer. The resulting viscous suspension can be used directly or may be used after it was emulsified in water.

(b) Aqueous Suspension

The following components were prepared: 25 wt % of compound selected from compounds 151-160; 3 wt % hydrate attapulagit; 10 wt % calcium lignosulphonate; 0.5 wt % sodium dihydrogen phosphate; and 61.5 wt % water. All of the components were ground in a ball mill until the particle size of the solid particles was reduced to less than about 10 micrometer. The aqueous suspension can be used directly.

(c) Bait formulation

The following components were prepared: 0.1-10 wt % of compound selected from compounds 244-251; 80 wt % wheat flour; and 19.9-10 wt % molasses. All of the components were sufficiently mixed and shaped according to the need. The edible bait can be applied to, for example, domestic or industrial places (such as kitchen, hospital, store and outdoor area) that were invaded by public health insects so as to kill and prevent the insects via oral ingestion.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be within the scope of the invention defined by the appended claims of the application.

We claim:

1. A compound represented by formula (A), or the optical isomer, cis-trans isomer, or insecticidal acceptable salt thereof,

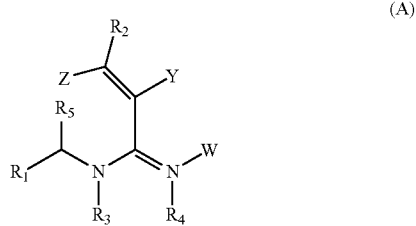

(A)

wherein:

R₁ is an unsubstituted or halogenated 5 or 6 membered heterocycle interrupted by nitrogen, oxygen and/or sulfur atom(s), or substituted or unsubstituted phenyl, and the substituents are one or more groups selected from halogen atom, $C_{1-4}$ haloalkyl and $C_{1-4}$ chloroalkoxyl;

R₂ is a hydrogen atom, $C_{1-6}$ alkyl, or $C_{1-6}$ alkyl substituted by fluoro, chloro or bromo;

R₃ and R₄ are independently selected from hydrogen atom, $C_{1-6}$ alkyl, allyl, benzyl, $C_{1-4}$ alkoxyl-$C_{1-4}$ alkyl, $C_{1-4}$ alkoxyl-carbonyl, phenoxylcarbonyl, $C_{2-6}$ alkynyl-carbonyl, $C_{2-3}$ alkenyl-carbonyl, $C_{3-6}$ cycloalkyl-carbonyl, furan carbonyl, N,N-dimethyl carbonyl, unsubstituted benzoyl or benzoyl substituted by one or more groups selected from halogen atom, $C_{1-4}$ alkyl, $C_{1-4}$ haloalkyl, $C_{1-4}$ alkoxyl, and $C_{1-4}$ alkyl-carbonyl, or R₃ and R₄ taken together forms a —CH₂—CH₂— or —CH₂—CH₂—CH₂—;

R₅ is a hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;

W is absent, or while R₃ and R₄ taken together forms —CH₂—CH₂— or —CH₂—CH₂—CH₂—, W is R₆ which forms onium salt with X⁻ by the nitrogen atom connected with R₆, wherein R₆ is a hydrogen atom, saturated or unsaturated $C_{1-6}$ hydrocarbon group, or saturated unsaturated halogenated $C_{1-6}$ hydrocarbon group, or saturated or unsaturated $C_{1-6}$ alkoxyl;

X⁻ is F⁻, Cl⁻, Br⁻, I⁻, $NO_3^-$, $SO_4^-$, AcO⁻, or PhCOO⁻;

Y is a nitro or cyano group;

Z is substituted or unsubstituted phenyl, substituted or unsubstituted 5 or 6 membered heterocycle interrupted by nitrogen, oxygen and/or sulfur atom(s), or substituted or unsubstituted $C_{5-12}$ heteroaryl, wherein the substituents are one or more groups selected from:

halogen atom, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl, or phenyl substituted by one or more groups selected from:

halogen atom, $C_{1-4}$ alkyl, $C_{1-4}$ haloalkyl, $C_{1-4}$ alkoxyl, $C_{1-4}$ alkyl-carbonyl, $C_{1-4}$ alkylamino and $C_{1-4}$ alkoxyl-carbonyl.

2. The compound according to claim 1, or the optical isomer, cis-trans isomer, or insecticidal acceptable salt thereof, wherein the compound is represented by one of the following formulas:

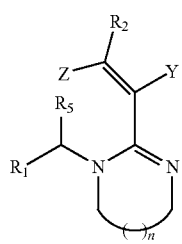

(I)

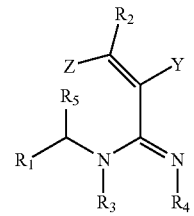

(II)

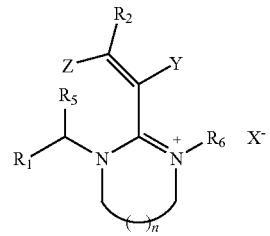

(III)

wherein R₁ is an unsubstituted or halogenated 5 or 6 membered heterocycle interrupted by nitrogen, oxygen and/or sulfur atom(s), or substituted or unsubstituted phenyl, and the substituents are one or more groups selected from halogen atom, $C_{1-4}$ haloalkyl and $C_{1-4}$ chloroalkoxyl;

R₂ is a hydrogen atom, $C_{1-6}$ alkyl, or $C_{1-6}$ alkyl substituted by fluoro, chloro or bromo;

R₃ and R₄ are independently selected from hydrogen atom, $C_{1-6}$ alkyl, allyl, benzyl, $C_{1-4}$ alkoxyl-$C_{1-4}$ alkyl, $C_{1-4}$ alkoxyl-carbonyl, phenoxylcarbonyl, $C_{2-6}$ alkynyl-carbonyl, $C_{2-3}$ alkenyl-carbonyl, $C_{3-6}$ cycloalkyl-carbonyl, furan carbonyl, N,N-dimethyl carbonyl, unsubstituted benzoyl or benzoyl substituted by one or more groups selected from halogen atom, $C_{1-4}$ alkyl, $C_{1-4}$ haloalkyl, $C_{1-4}$ alkoxyl, and $C_{1-4}$ alkyl-carbonyl, or R₃ and R₄ taken together forms a —CH₂—CH₂— or —CH₂—CH₂—CH₂—;

R₅ is a hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;

R₆ is a hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;

X⁻ is F⁻, Cl⁻, Br⁻, I⁻, $NO_3^-$, $SO_4^-$, AcO⁻, or PhCOO⁻;

Y is a nitro or cyano group;

Z is substituted or unsubstituted phenyl, substituted or unsubstituted 5 or 6 membered heterocycle interrupted by nitrogen, oxygen and/or sulfur atom(s), or substituted or unsubstituted $C_{5-12}$ heteroaryl, wherein the substituents are one or more groups selected from:

halogen atom, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl, or phenyl substituted by one or more groups selected from:

halogen atom, $C_{1-4}$ alkyl, $C_{1-4}$ haloalkyl, $C_{1-4}$ alkoxyl, $C_{1-4}$ alkyl-carbonyl, $C_{1-4}$ alkylamino and $C_{1-4}$ alkoxyl-carbonyl, and n represents 0 or 1.

3. The compound according to claim 1, or the optical isomer, cis-trans isomer, or insecticidal acceptable salt thereof, wherein R₁ represents unsubstituted or halogenated groups selected from pyridyl, thiazolyl, pyrimidinyl, tetrahydrofuryl, and oxazolyl.

4. The compound according to claim 1, or the optical isomer, cis-trans isomer, or insecticidal acceptable salt thereof, wherein $R_2$ represents hydrogen atom or $C_{1-6}$ alkyl.

5. The compound according to claim 1, or the optical isomer, cis-trans isomer, or insecticidal acceptable salt thereof, wherein $R_3$ and $R_4$ are hydrogen atom or $C_{1-6}$ alkyl.

6. The compound according to claim 1, or the optical isomer, cis-trans isomer, or insecticidal acceptable salt thereof, wherein $R_5$ represents hydrogen atom or $C_{1-6}$ alkyl.

7. The compound according to claim 1, or the optical isomer, cis-trans isomer, or insecticidal acceptable salt thereof, wherein $R_6$ represents hydrogen atom, saturated or unsaturated $C_{1-3}$ hydrocarbon group, saturated or unsaturated halogenated $C_{1-3}$ hydrocarbon group, saturated or unsaturated $C_{1-3}$ alkoxyl; and $X^-$ represents $F^-$, $Cl^-$, $Br^-$, $NO_3^-$, $SO_4^-$, $AcO^-$, or $PhCOO^-$.

8. The compound according to claim 1, or the optical isomer, cis-trans isomer, or insecticidal acceptable salt thereof, wherein Z represents substituted or unsubstituted furyl, thienyl, pyrrolyl, imidazolyl, thiazolyl, or oxazolyl, and wherein the substituents are selected from halogen atom, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl, and phenyl substituted by one or more groups selected from:
halogen atom, $C_{1-4}$ alkyl, $C_{1-4}$ haloalkyl, $C_{1-4}$ alkoxyl, $C_{1-4}$ alkyl-carbonyl, $C_{1-4}$ alkylamino, and $C_{1-4}$ alkoxyl-carbonyl.

9. An insecticidal composition, which comprises:
(a) 0.001 wt %-99.99 wt % the compound according to claim 1, or the optical isomer, cis-trans isomer, or insecticidal acceptable salt thereof, or the combinations thereof; and
(b) insecticidal acceptable carrier(s) and/or excipient(s).

10. The composition according to claim 9, wherein said composition is used to kill or control the insects chosen from: Coleoptera, Lepidoptera, Hemiptera, Orthoptera, Isoptera or dipteral insects, more preferably Isoptera or Lepidoptera insects.

11. An insecticidal and/or insect controlling method which comprises the step of applying the insecticidal composition according to claim 10 to plants, the surrounding fields or the environment thereof that are being attacked or possibly to be attacked by insects.

12. A method for the preparation of the compound claim 1, or the optical isomer, cis-trans isomer, or insecticidal acceptable salt thereof, wherein the method comprises the steps of:
in presence of catalytic amount of acid, reacting a compound of formula (a) with an aldehyde of formula (b) or a ketone of formula (c) at 0-60° C. to obtain the compound of formula (A),

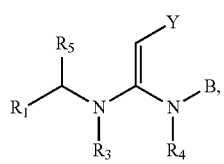
(a)

Z—CHO, (b)

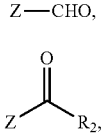
(c)

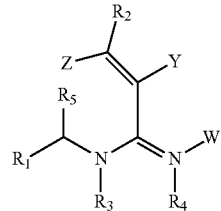
(A)

wherein, $R_1$ is an unsubstituted or halogenated 5 or 6 membered heterocycle interrupted by nitrogen, oxygen and/or sulfur atom(s), or substituted or unsubstituted phenyl, and the substituents are one or more groups selected from halogen atom, $C_{1-4}$ haloalkyl and $C_{1-4}$ chloroalkoxyl;

$R_2$ is a hydrogen atom, $C_{1-6}$ alkyl, or $C_{1-6}$ alkyl substituted by fluoro, chloro or bromo;

$R_3$ and $R_4$ are independently selected from hydrogen atom, $C_{1-6}$ alkyl, allyl, benzyl, $C_{1-4}$ alkoxyl-$C_{1-4}$ alkyl, $C_{1-4}$ alkoxyl-carbonyl, phenoxylcarbonyl, $C_{2-6}$ alkynyl-carbonyl, $C_{2-3}$ alkenyl-carbonyl, $C_{3-6}$ cycloalkyl-carbonyl, furan carbonyl, N,N-dimethyl carbonyl, unsubstituted benzoyl or benzoyl substituted by one or more groups selected from halogen atom, $C_{1-4}$ alkyl, $C_{1-4}$ haloalkyl, $C_{1-4}$ alkoxyl, and $C_{1-4}$ alkyl-carbonyl, or $R_3$ and $R_4$ taken together forms a —$CH_2$—$CH_2$— or —$CH_2$—$CH_2$—$CH_2$—;

$R_5$ is a hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;

W is absent, or while $R_3$ and $R_4$ taken together forms —$CH_2$13 $CH_2$— or —$CH_2$—$CH_2$—$CH_2$—, W is $R_6$ which forms onium salt with $X^-$ by the nitrogen atom connected with $R_6$, $R_6$ is a hydrogen atom, saturated or unsaturated $C_{1-6}$ hydrocarbon group, saturated or unsaturated halogenated $C_{1-6}$ hydrocarbon group, or saturated or unsaturated $C_{1-6}$ alkoxyl;

$X^-$ is $F^-$, $Cl^-$, $Br^-$, $NO_3^-$, $SO_4^-$, $AcO^-$, or $PhCOO^-$

Y is a nitro or cyano group;

Z is substituted or unsubstituted phenyl, substituted or unsubstituted 5 or 6 membered heterocycle interrupted by nitrogen, oxygen and/or sulfur atom(s), or substituted or unsubstituted $C_{5-12}$ heteroaryl, wherein the substituents are one or more groups selected from:
halogen atom, nitro, $C_{1-6}$ alkyl, hydroxyl $C_{1-6}$ alkyl, hydroxyl, $C_{1-6}$ alkoxyl, amino, $C_{1-6}$ alkylamino, unsubstituted phenyl, or phenyl substituted by one or more groups selected from:
halogen atom, $C_{1-4}$ alkyl, $C_{1-4}$ haloalkyl, $C_{1-4}$ alkoxyl, $C_{1-4}$ alkyl-carbonyl, $C_{1-4}$ alkylamino and $C_{1-4}$ alkoxyl-carbonyl, B represents hydrogen atom or $R_6$;

provided that when W exists in the compound of formula (A) and represents $R_6$, the method further comprises the step of forming an onium salt by further reacting with an acid comprising $X^-$.

13. The method according to claim 12, wherein the compound has the structure of formula (I), (II) or (III), and the preparation thereof includes the following steps:

in the presence of catalytic amount of acid, carrying out the following reaction in acetonitrile at 20-30° C. for 2-24 hours to obtain the compound of formula (I):

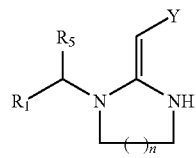 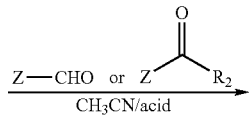

(I)

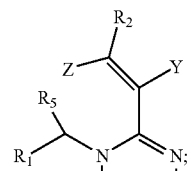

in the presence of catalytic amount of acid, carrying out the following reaction in acetonitrile at 20-30° C. for 2-24 hours to obtain the compound of formula (II):

(II)

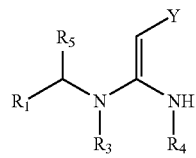 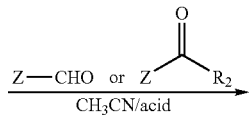

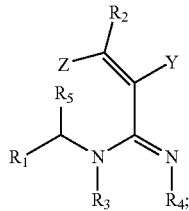

or in the presence of catalytic amount of acid, carrying out the following reaction in acetonitrile at 10-50° C. for 2-24 hours to obtain the compound of formula (III)

(III)

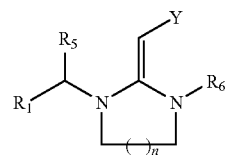 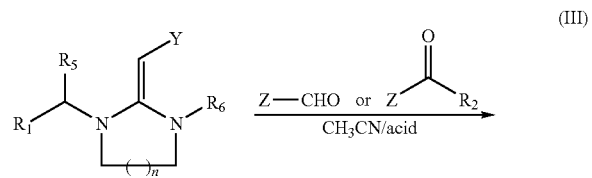

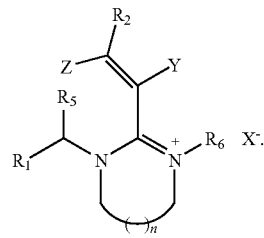

* * * * *